United States Patent [19]

Wan et al.

[11] Patent Number: 5,480,407
[45] Date of Patent: Jan. 2, 1996

[54] SUTURING INSTRUMENT WITH HEMORRHAGING CONTROL

[76] Inventors: Shaw P. Wan, 603 Lariat La., Rolla, Mo. 65401; Rosendo Martinez, 790 Prigge Rd., St. Louis, Mo. 63138

[21] Appl. No.: 264,515

[22] Filed: Jun. 23, 1994

Related U.S. Application Data

[63] Continuation-in-part of Ser. No. 992,494, Dec. 17, 1992, Pat. No. 5,342,374.

[51] Int. Cl.⁶ ........................... A61B 17/04; A61M 29/02
[52] U.S. Cl. ............................................. 606/148; 606/192
[58] Field of Search ..................................... 606/144, 148, 606/191, 192, 193, 194; 604/96, 104

[56] References Cited

U.S. PATENT DOCUMENTS

| | | |
|---|---|---|
| 659,422 | 10/1900 | Shidler . |
| 2,072,346 | 3/1937 | Smith ........................... 27/24 |
| 2,457,244 | 12/1948 | Lamson ........................ 604/96 |
| 2,544,282 | 3/1951 | Sinclair et al. ................ 223/101 |
| 2,547,758 | 4/1951 | Keeling ........................ 128/349 |
| 2,589,499 | 3/1952 | Lake ............................ 223/101 |
| 2,601,564 | 6/1952 | Smith ........................... 128/340 |
| 2,862,497 | 12/1958 | Pagano ........................ 604/96 |
| 2,897,820 | 8/1959 | Tauber ......................... 128/334 |
| 2,936,761 | 5/1960 | Snyder ......................... 604/96 |
| 3,833,003 | 9/1974 | Taricco ......................... 604/96 |
| 3,877,434 | 4/1975 | Ferguson et al. ............. 128/327 |
| 3,908,637 | 9/1975 | Doroshow .................... 128/2 F |
| 4,553,543 | 11/1985 | Amarasinghe ............... 128/334 R |
| 4,553,544 | 11/1985 | Nomoto et al. .............. 128/340 |
| 4,597,390 | 7/1986 | Mulhollan et al. ........... 128/340 |
| 4,784,139 | 11/1988 | Demos ......................... 128/340 |
| 4,848,367 | 7/1989 | Avant et al. ................... 128/898 |
| 4,873,977 | 10/1989 | Avant et al. ................... 128/334 R |
| 4,911,164 | 3/1990 | Roth ............................. 606/148 |
| 5,053,043 | 10/1991 | Gottesman et al. .......... 606/148 |
| 5,183,463 | 2/1993 | Debbas ........................ 604/96 |
| 5,201,744 | 4/1993 | Jones ........................... 606/148 |
| 5,342,374 | 8/1994 | Wan et al. .................... 606/148 |

OTHER PUBLICATIONS

Robert W. Taylor, A.M., M.D., A Practical Treatise on Genito-Uninary and Venereal Diseases and Syphillis, 1904.
Meredith Campbell, M.S., M.D., Urology Volume Two, F.A.C.S., 1954, pp. 940–941.
Joseph B. Daowd, and John J. Smith, III, MD, Urologic Clinics of North America, vol. 17, No. 3, Balloon Dilatation of the Prostate, Aug. 1990, pp. 671–677.
V. Muller, Urological Surgical Instruments, catalog, p. C5, 1988.

*Primary Examiner*—Tamara L. Graysay
*Attorney, Agent, or Firm*—Senniger, Powers, Leavitt & Roedel

[57] ABSTRACT

A suturing instrument for impeding the flow of blood around a suturing site comprises a substantially rigid shaft having opposite ends which are distal and proximal relative to a person holding the instrument, an expansible annular member of flexible, resilient material encircling the shaft adjacent its distal end, and an expansion mechanism for expanding the annular member radially outwardly relative to the shaft to impede the flow of blood around a suturing site. The distal end of the shaft is adapted to be inserted into a patient during the suturing procedure.

22 Claims, 29 Drawing Sheets

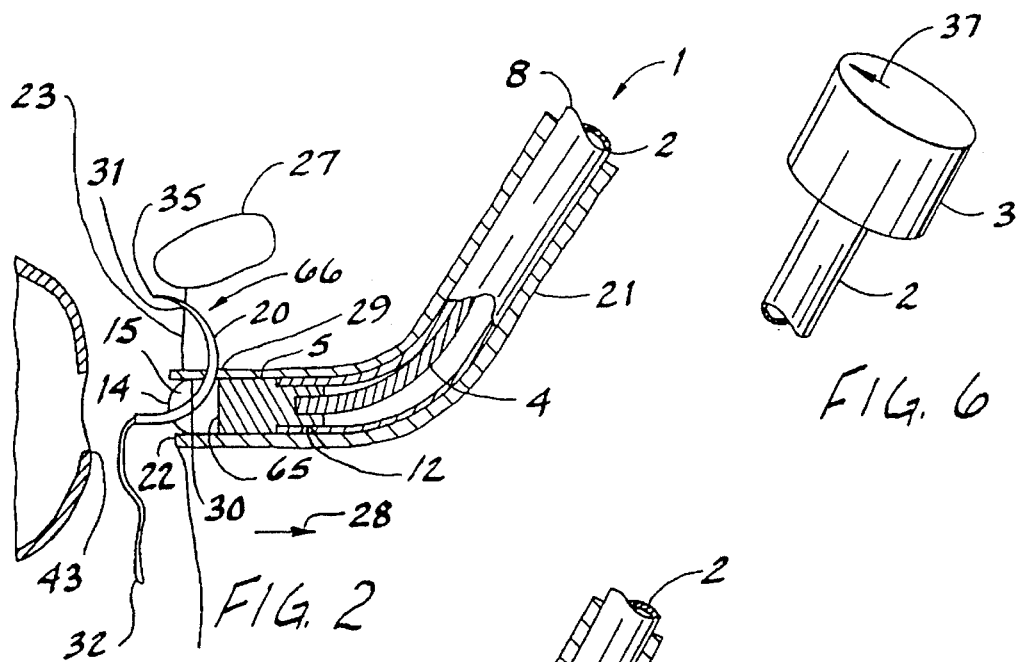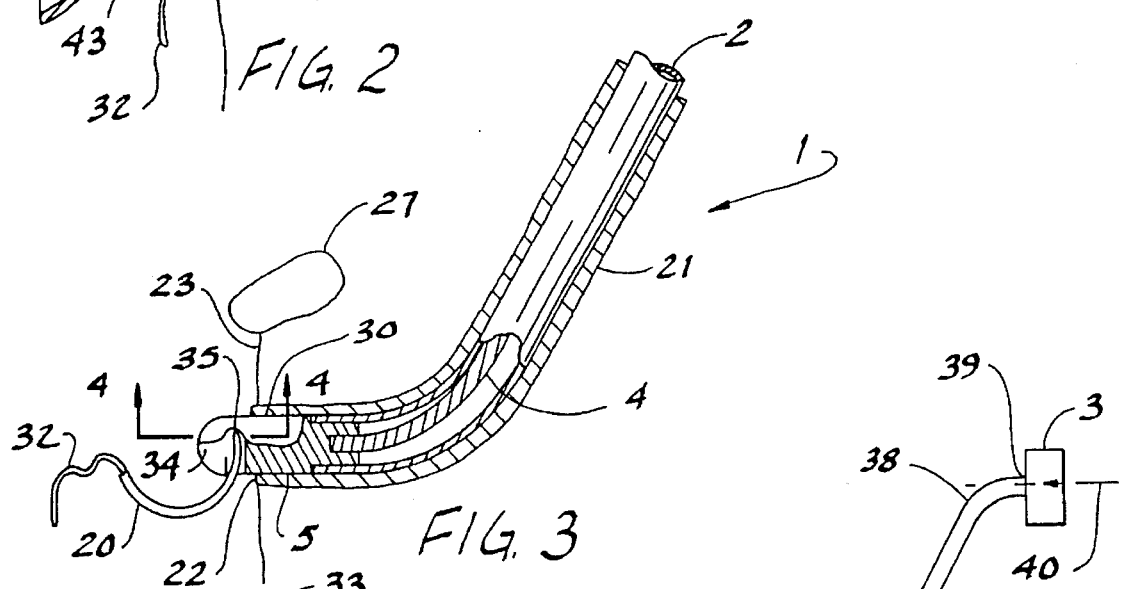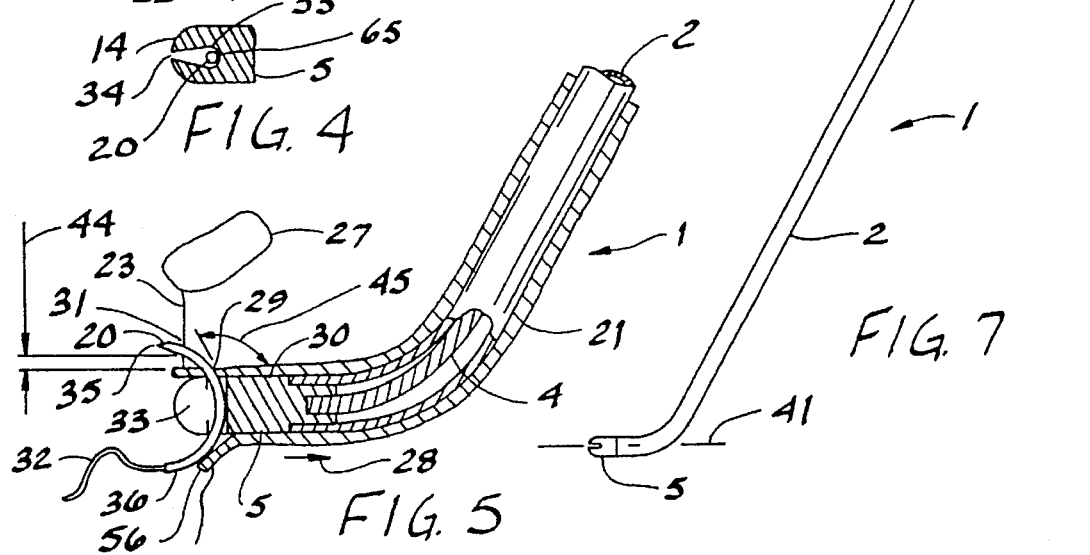

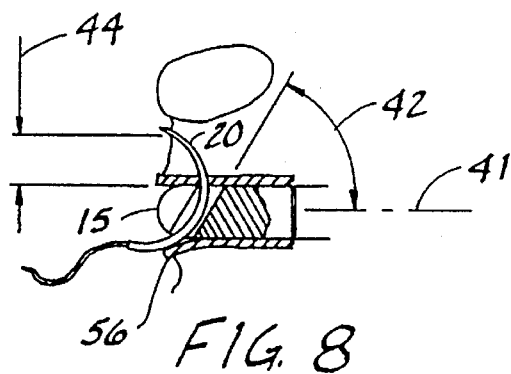
FIG. 8
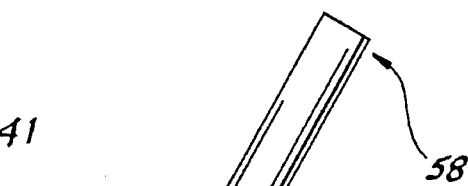
FIG. 10B
FIG. 10A
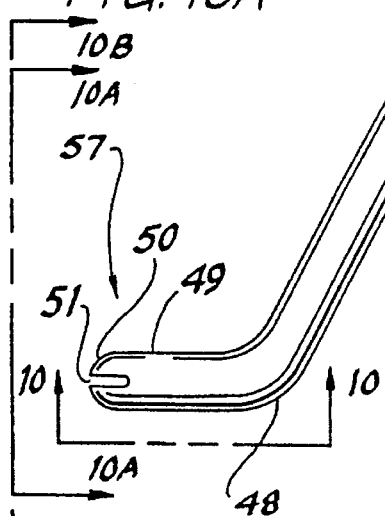
FIG. 9
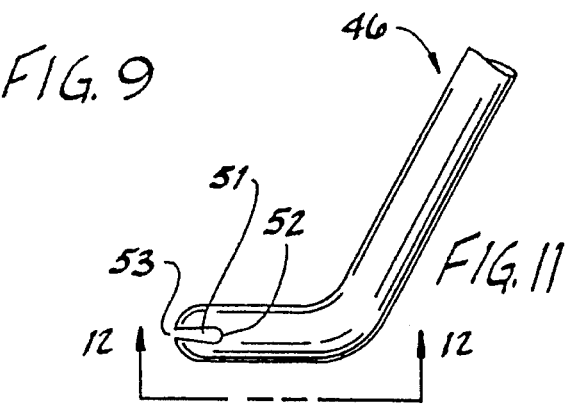
FIG. 11
FIG. 10
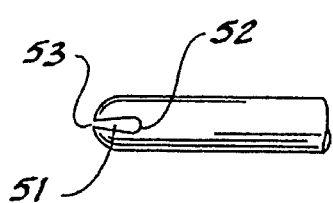
FIG. 12

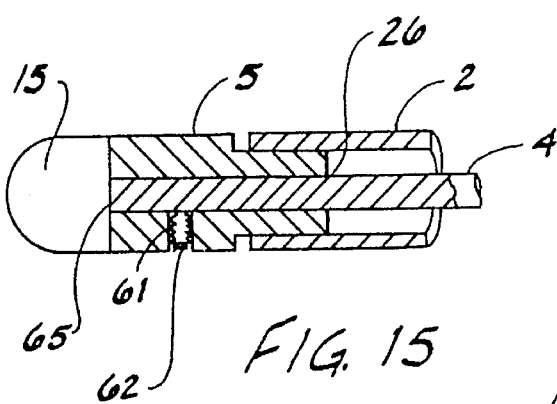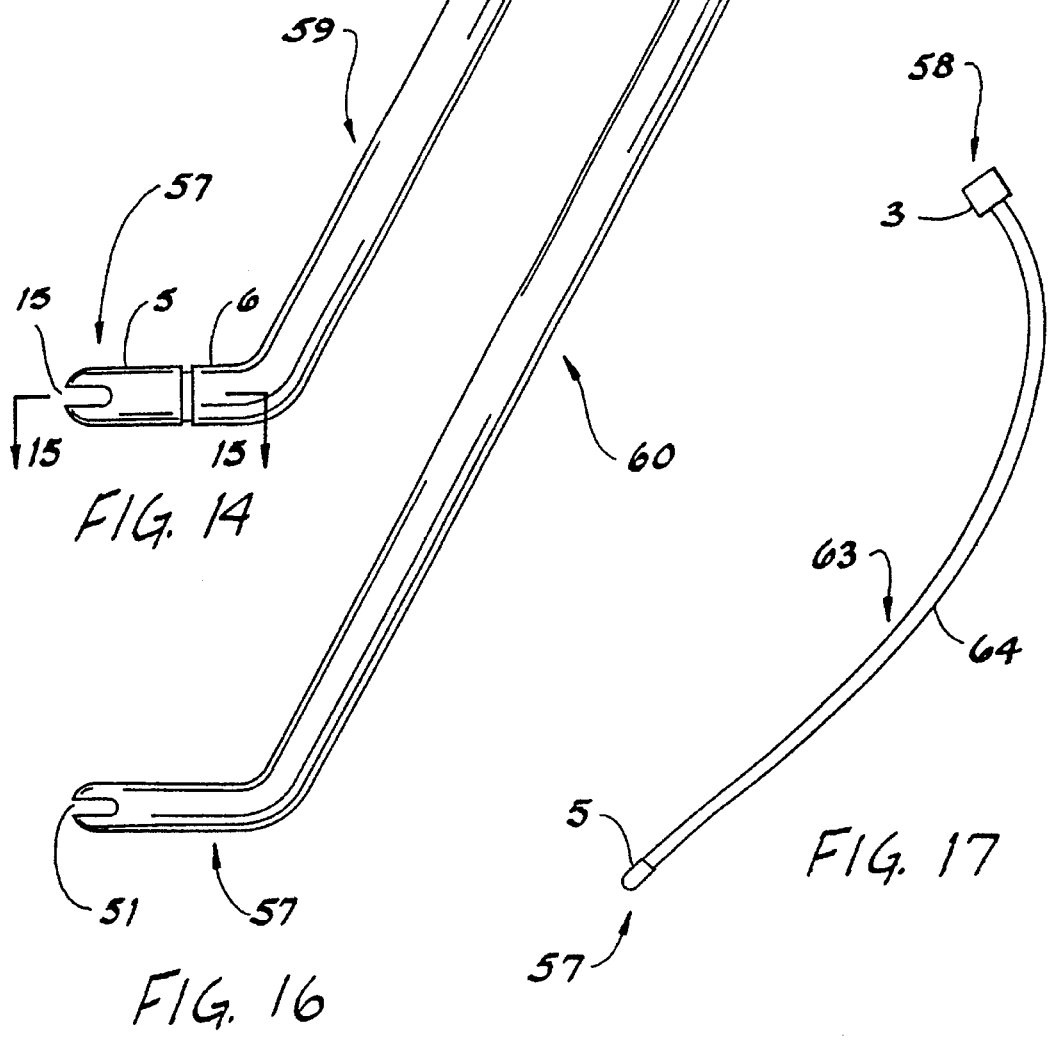

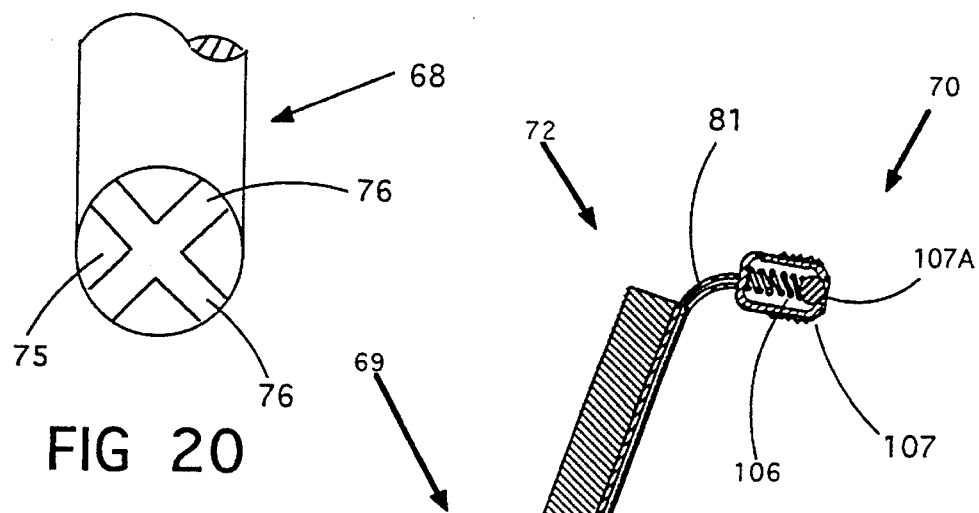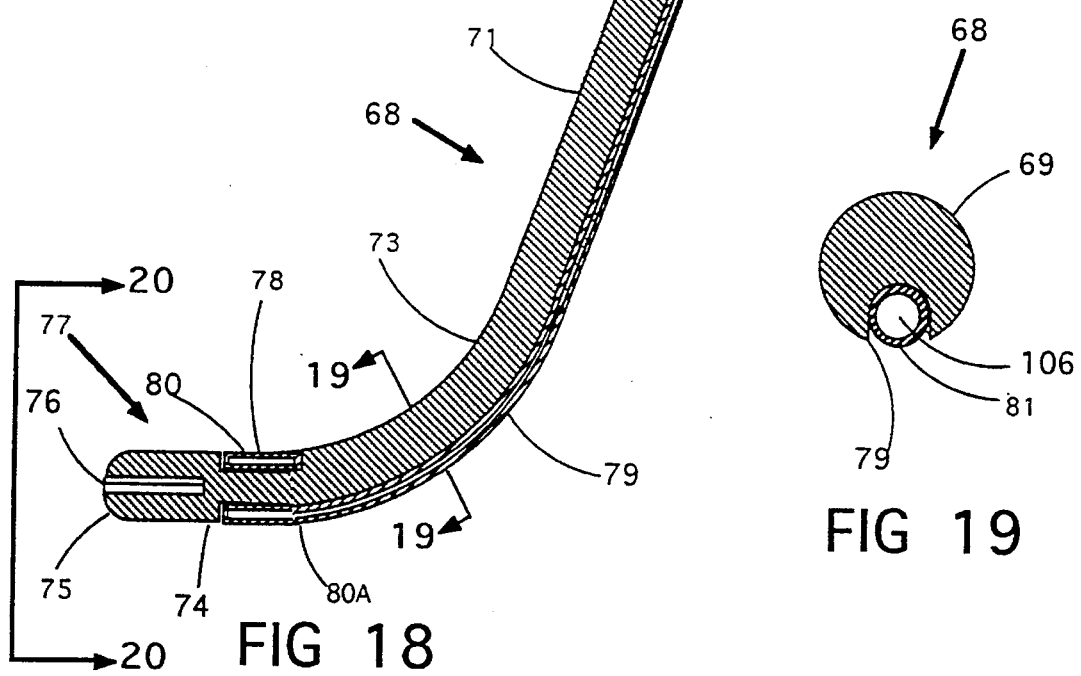

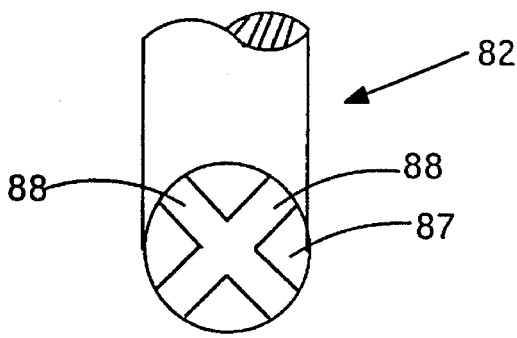
FIG 22
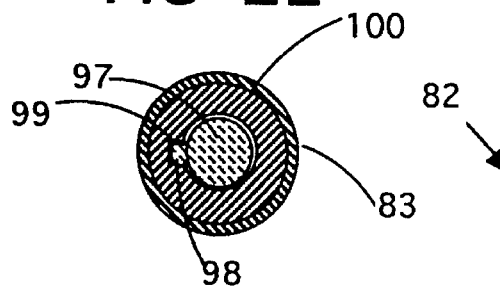
FIG 23
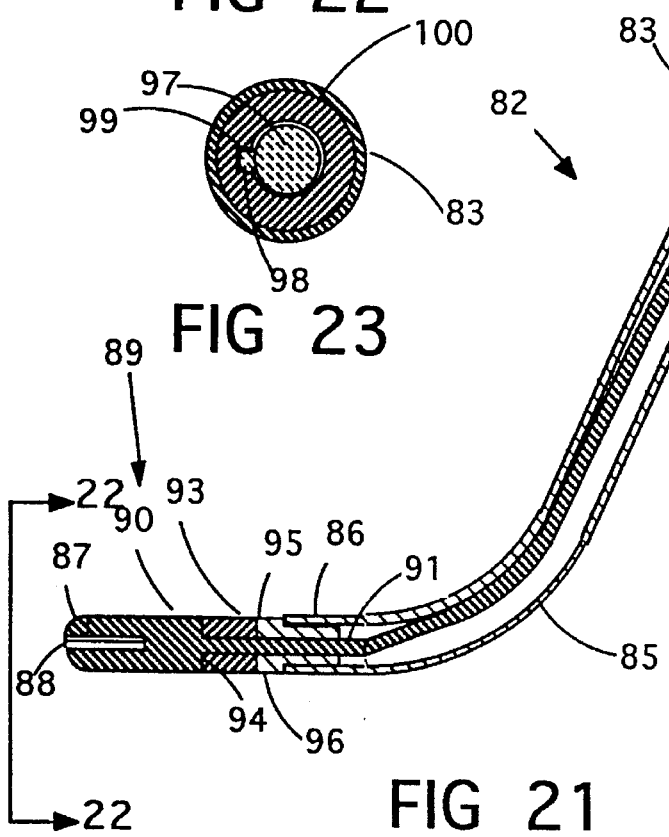
FIG 21
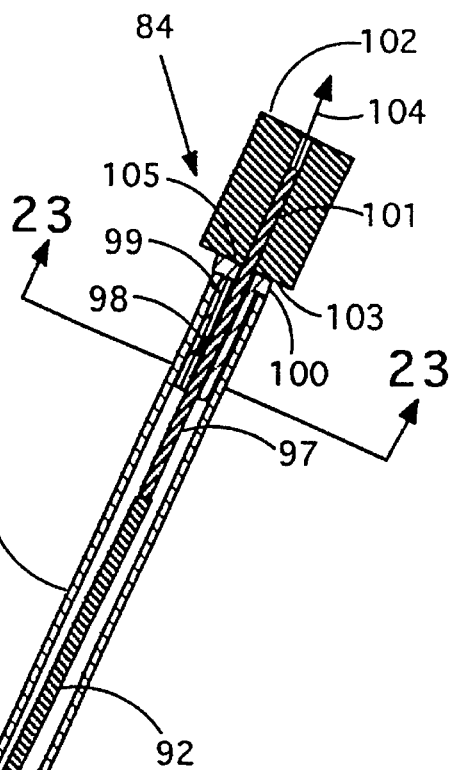

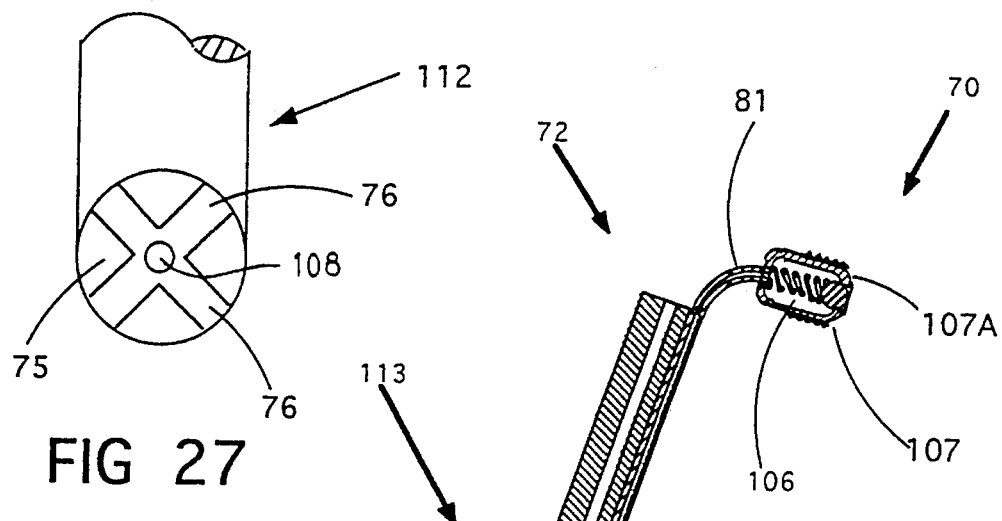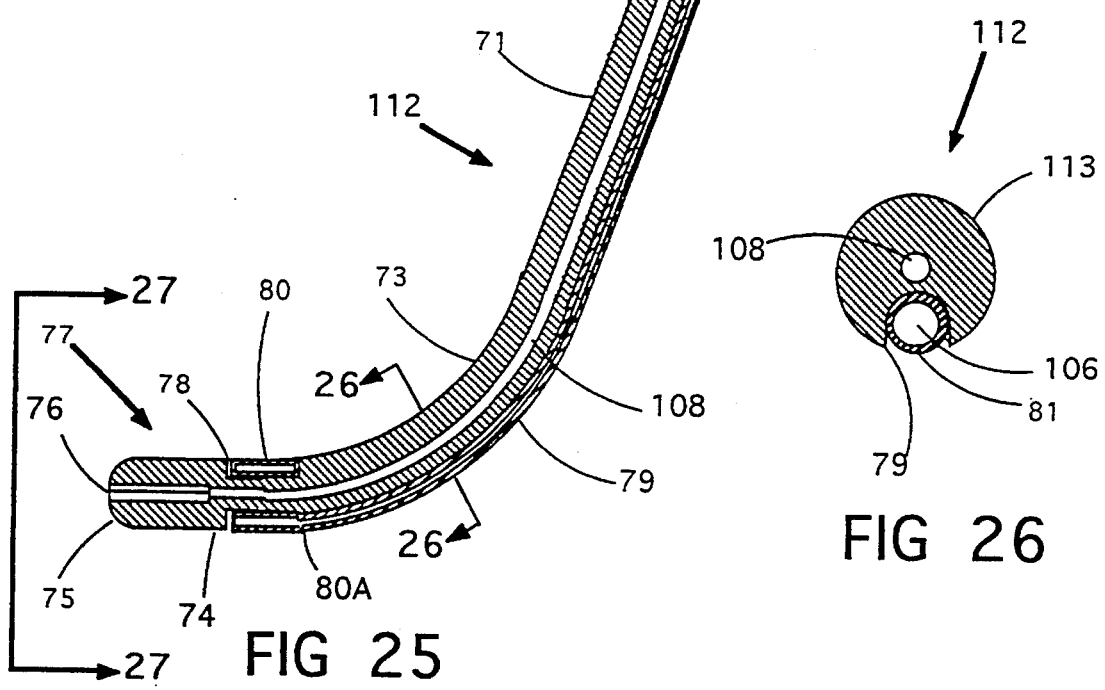

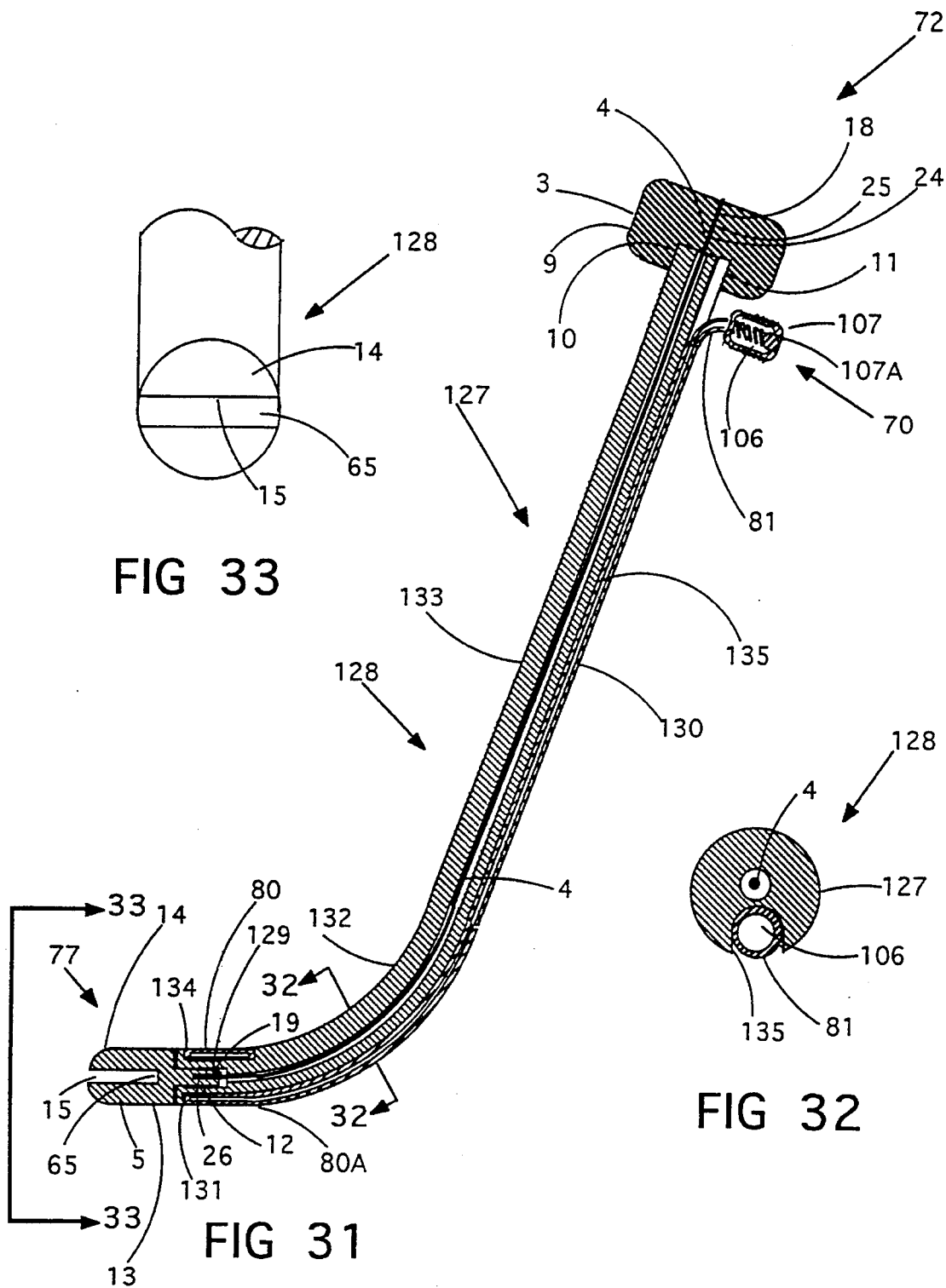

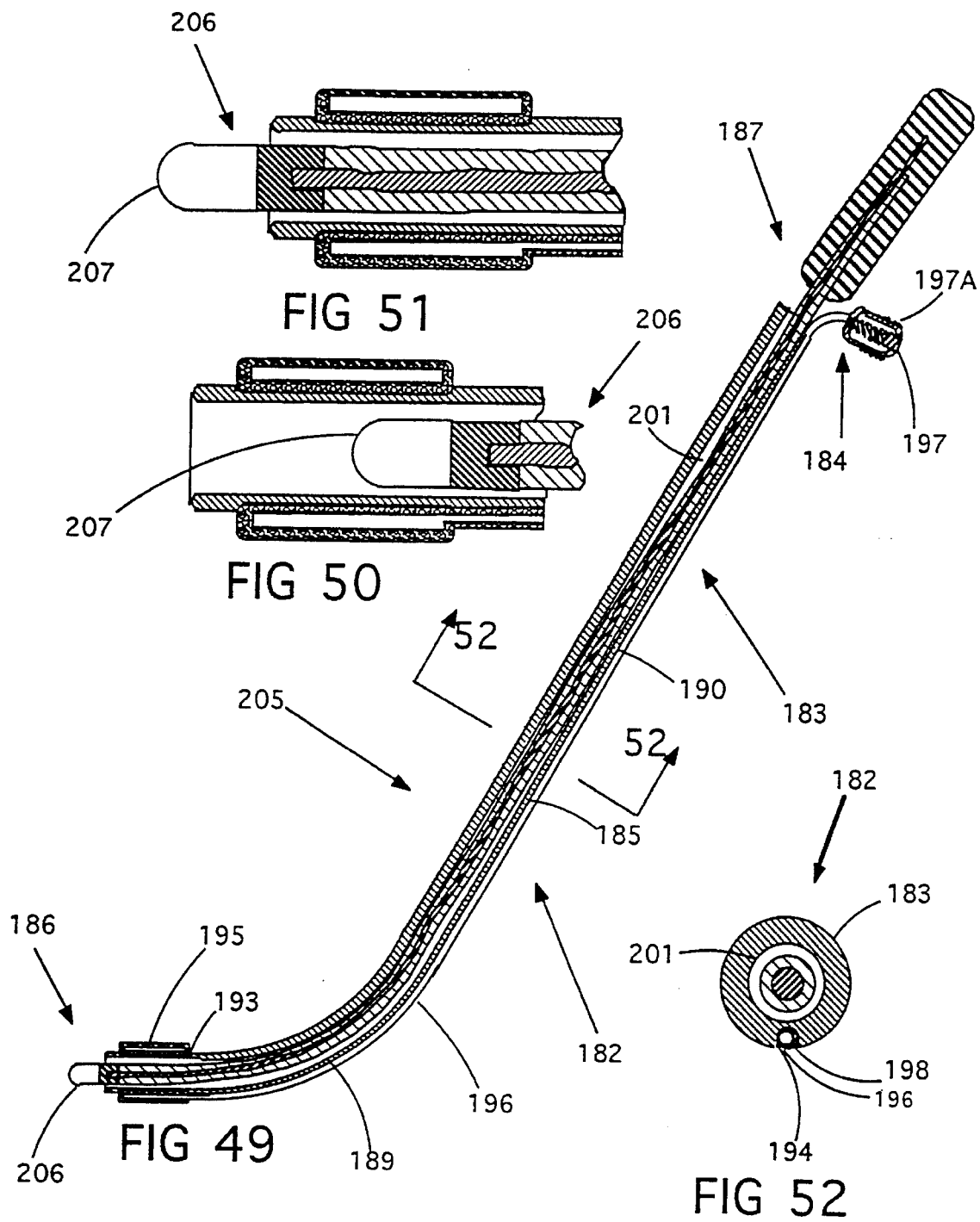

SUTURING INSTRUMENT WITH HEMORRHAGING CONTROL

This is a continuation-in-part of U.S. patent application Ser. No. 07/992,494 now U.S. Pat. No. 5,342,374 filed Dec. 17, 1992 for a suture guiding device and method of use, the aforesaid application being incorporated herein by reference.

BACKGROUND OF INVENTION

The present invention relates to a suturing instrument and, more particularly, to a suturing instrument for impeding the flow of blood around a suturing site during a radical prostatectomy or while anastomosing two tubular structures.

The suturing instrument of this invention represents an improvement over the suture guiding device disclosed in applicant's co-pending patent application Ser. No. 07/992,494 now U.S. Pat. No. 5,342,374. The latter instrument has a shaft with a suture guide at the distal end thereof for guiding a suture needle during a radical prostatectomy procedure or while anastomosing two tubular structures. While this instrument has proven to be satisfactory, a continuing problem with these procedures is the hemorrhaging of the severed dorsal vein complex and bleeding of the urethral stump during the suturing procedures.

Prior suture guiding devices and the guide disclosed in the co-pending application do not assist in the stoppage of bleeding during such suturing procedures.

SUMMARY OF THE INVENTION

Among the several objects of this invention may be noted the provision of a suture instrument to impede the flow of blood around a suturing site; the provision of such an instrument which is particularly useful during a radical prostatectomy or anastomosing two tubular structures; the provision of such an instrument which applies pressure to the dorsal vein complex and the lateral vascular bundle to help stop the hemorrhaging of the severed dorsal vein complex and bleeding of the urethral stump during suturing procedures; the provision of such an instrument which will cause eversion of the urethral stump to facilitate placement of sutures; the provision of such an instrument which includes a suture guide for guiding a suture needle; and the provision of such an instrument which allows insertion of other medical implements therethrough for use in the suturing procedure.

Generally, a suturing instrument of the present invention is used to impede the flow of blood around a suturing site. The suturing instrument comprises a substantially rigid shaft having opposite ends which are distal and proximal relative to a person holding the instrument, the distal end of the shaft being adapted to be inserted into a patient during the procedure. The instrument further includes an expansible annular member of flexible, resilient material encircling the shaft adjacent its distal end and expansion means for expanding the annular member radially outwardly relative to the shaft to impede the flow of blood around a suturing site.

A second aspect of the present invention comprises a system for impeding the flow of blood around a suturing site. The system comprises a suturing instrument and an obturator. The suturing instrument includes a shaft having opposite ends which are distal and proximal relative to a person holding the instrument, the distal end of the shaft being adapted to be inserted into a patient during a suturing procedure. The suturing instrument further has a passageway in the shaft extending the full length of the shaft, an expansible annular member of flexible, resilient material encircling the shaft adjacent its distal end, and expansion means for expanding the annular member radially outwardly relative to the shaft to impede the flow of blood around a suturing site. The obturator of the suturing system includes an elongate, flexible shaft having opposite ends which are distal and proximal relative to a person holding the obturator, a handle mounted on the shaft of the obturator generally adjacent its proximal end, and a suture guide mounted on the shaft of the obturator at its distal end. The suture guide of the obturator has at least one outwardly opening, generally channel-shaped end slit extending endwise proximally inwardly from the distal end of the shaft and laterally across the guide from one side of the guide to an opposite side of the guide. The end slit has a guide surface configured for guiding a suture needle pulling a suture thread as it passes through said guide from one side of the guide to an opposite side of the guide. The shaft of the obturator is adapted for insertion, distal end first, through the passageway of the suturing instrument to a position in which the suture guide extends distally beyond the distal end of the shaft of the suturing instrument. The handle is in a position where it may be manipulated to effect rotation of the suture guide relative to the suturing instrument about an axis extending endwise with respect to the distal end of the suturing instrument to selectively adjust the suture-guiding position of said guide surface.

Other objects and features will be in part apparent and in part pointed out hereinafter.

BRIEF DESCRIPTION OF THE DRAWINGS

FIG. 2 is a sectional view of a portion of the suture guiding device of FIG. 1 showing the device as used in a suturing procedure.

FIG. 3 is a sectional view similar to FIG. 2 showing an alternative embodiment of the device incorporating a suture guide with needle pulling means.

FIG. 4 is a sectional view of the suture guide shown in FIG. 3.

FIG. 5 is a view similar to FIG. 3 illustrating a continuation of the procedure in FIG. 3.

FIG. 6 is an isometric view of a portion of a suture guiding device of FIG. 1 showing an alternative design.

FIG. 7 is a side view of an alternative embodiment of the device in FIG. 1.

FIG. 8 is a sectional view of an alternative embodiment of the device shown in FIGS. 3 and 5.

FIG. 9 is a side view of a one piece suture guiding device of this invention.

FIG. 10 is a side view of the device in FIG. 9.

FIG. 10A is an end view of the device in FIG. 9.

FIG. 10B is an end view similar to FIG. 10A but showing an alternative slit design.

FIG. 11 is a side view of an alternative embodiment of the device in FIG. 9.

FIG. 12 is a side view of the device in FIG. 11.

FIG. 14 is a reversible, externally controlled, rotational suture guiding device with slit and needle pulling means.

FIG. 15 is an enlarged sectional view of a portion of the device in FIG. 14.

FIG. 16 is a one-piece reversible suture guiding device with slit and needle pulling means.

FIG. 17 is a flexible, externally controlled, rotational suture guiding device.

FIG. 18 is a vertical section of a suturing instrument with hemorrhaging control of the present invention.

FIG. 19 is a sectional view taken along line 19—19 of FIG. 18.

FIG. 20 is a partial end view of the suturing instrument shown in FIG. 18.

FIG. 21 is a vertical section of another embodiment of the suture instrument with hemorrhaging control of the present invention.

FIG. 22 is a partial end view of the suturing instrument shown in FIG. 21.

FIG. 23 is a sectional view taken along line 23—23 of FIG. 21.

FIG. 25 is a vertical section of another embodiment of a suturing instrument with hemorrhaging control.

FIG. 26 is a sectional view taken along line 26—26 of FIG. 25.

FIG. 27 is a partial end view of the instrument shown in FIG. 25.

FIG. 31 is a vertical section of another embodiment of the suturing instrument with hemorrhaging control of the present invention.

FIG. 32 is a sectional view taken along line 32—32 of FIG. 31.

FIG. 33 is a partial end view of the instrument shown in FIG. 31.

FIG. 49 is a vertical section of the obturator shown in FIG. 48 being used with the suturing instrument shown in FIG. 44.

FIG. 50 is an enlarged partial vertical section of the instrument shown in FIG. 49 prior to inflation of an expansible member and while the obturator shown in FIG. 45 is retracted.

FIG. 51 is an enlarged partial vertical section of the suturing instrument shown in FIG. 49, after inflation of the expansible member and while the suture guiding instrument shown of FIG. 48 is advanced distally.

FIG. 52 is a sectional view taken along line 52—52 of FIG. 49.

Corresponding reference characters indicate corresponding parts throughout the several views of the drawings.

DETAILED DESCRIPTION OF THE DRAWINGS

Figure 1:
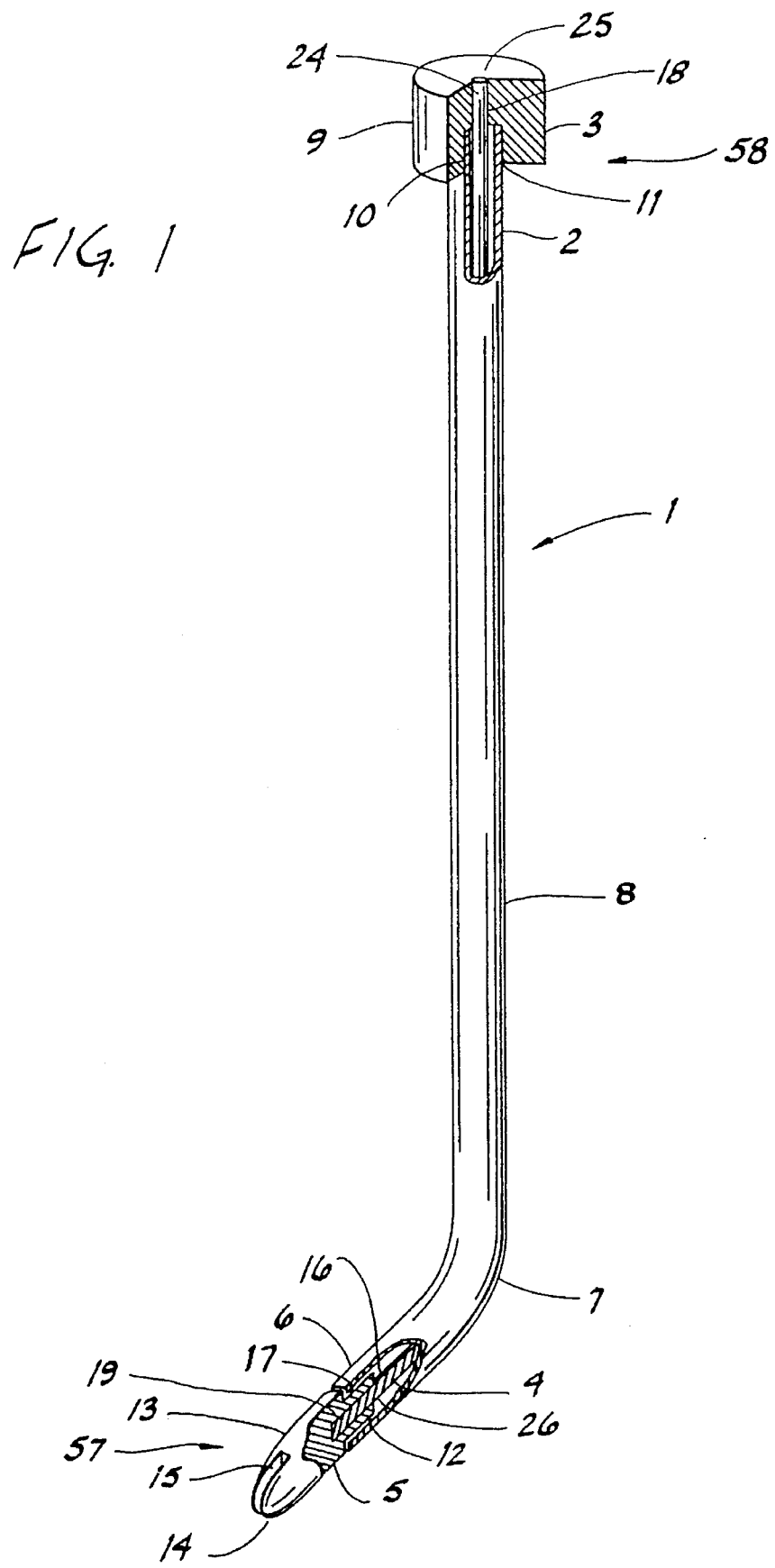
FIG. 1 is an isometric view of an externally controlled, rotational suture guiding device of the present invention.

Referring now in more detail to the drawings which illustrate practical embodiments of the present invention, FIG. 1 shows an externally controlled, rotational suture guiding device, generally designated 1.

As shown in FIG. 1, the externally controlled, rotational suture guiding device 1 comprises a tubular shaft 2 having opposite ends which are distal 57 and proximal 58 relative to a person holding the device for use in a suturing procedure, the distal end 57 of the shaft being adapted to be inserted into a patient during the procedure. The device 1 further comprises a suture guide 5 mounted at the distal end 57 of the tubular shaft 2 for rotation relative to the tubular shaft 2 about an axis extending endwise with respect to the tubular shaft 2, a control knob 3 at the proximal end 58 and means comprising a flexible shaft 4 interconnecting the suture guide 5 and the control knob 3.

The tubular shaft 2 has a short, straight tubular distal section 6, followed by a curved tubular section 7, followed by a long, straight tubular section 8. When the suture guiding device 1 is in use, the tubular shaft 2 must be capable of being manually grasped at the long, straight tubular section 8, and kept in control by the surgeon while inserted into the urethral meatus and guided all the way through the urethra 21 to eventually protrude out of the urethral stump 22 in the same manner as a standard urethral sound is used.

The control knob 3 consists of a member 9 with a counterbore 10 and a small diameter hole 25. The counterbore 10 has to be capable of spinning around end 11 of tubular shaft 2. The counterbore 10 has to be deep enough to support and stabilize control knob 3 on end 11 of tubular shaft 2. The small hole 25 is the portion of the control knob 3 that accepts and holds flexible shaft 4.

Suture guide 5 is an elongated member extending axially with respect to distal end portion 6 of the tubular shaft. The guide 5 has a smaller diameter proximal end portion 12 with a small hole 26 extending axially of the guide, a larger diameter middle portion 13, and a blunt distal end portion 14. A generally channel-shaped slit 15 is formed in the blunt end portion 14 and extends into the larger diameter middle portion 13. The slit 15 is wide enough to allow passage of a curved needle 20 through the blunt end portion 14 and into the middle shaft portion 13. As shown in FIG. 1 and 2, the slit 15 has an open mouth, generally parallel side walls and a bottom surface or floor 65 which extends generally perpendicular to the longitudinal axis of the guide 5.

End 24 of flexible shaft 4 is attached at 18 firmly inside hole 25 of control knob 3. The shaft 4 extends through the tubular shaft 2 and is attached at 19 firmly inside hole 26 of suture guide 5.

Small diameter proximal end portion 12 of suture guide 5 is capable of spinning inside end 17 of tubular shaft 2. The proximal end portion 12 of suture guide 5 must be long enough to support and stabilize itself inside end 17 of tubular shaft 2.

As it can be seen, when control knob 3 is manually rotated, the flexible shaft 4 is capable of transmitting the rotation to the suture guide 5. This rotation allows the slit 15 in the guide to be oriented at any location around the urethral stump 22 during a radical prostatectomy procedure or tubular anastomosis.

As shown in FIG. 2, when a surgeon is uniting the bladder neck 43 to the urethral stump 22, a curved needle 20 pulling a suture thread 32 has to be inserted through the urethral stump 22 and its surrounding tissue 23, without going through the pubic bone 27.

With our invention, the externally controlled, rotational suture guiding device 1 is inserted inside the urethra 21 in the same way as a standard urethral sound by inserting the blunt distal end portion 14 of the guide into the urethral meatus until the blunt end portion 14 protrudes out of the urethral stump 22. After the suture guiding device 1 is in place, the long straight tubular portion 8 of tubular shaft 2 is housed inside the penis and the suture guide 5 extends out through the urethral stump 22.

When the blunt distal end portion 14 is observed, control knob 3 is manually rotated by the surgeon. The rotation of control knob 3 will cause flexible shaft 4 to rotate, which will cause the small diameter proximal end portion 12 of the suture guide 5 to rotate inside the distal end 17 of tubular shaft 2.

The surgeon will be capable of controlling the rotation of the suture guide 5 until the slit 15 in the blunt end portion 14 is at the desired position of suture insertion. After the desired orientation of slit 15 is obtained, curved needle 20 is inserted inside the slit 15.

As can be observed, curved needle 20 is capable of being positioned in two different orientations 180 degrees apart. Therefore, two sutures can be placed with a single rotation of the suture guide 5.

After the curved needle 20 is placed inside slit 15, the suture guiding device 1 can be pulled back slightly 28 until the surgeon is capable of finding the desired location of needle entry 29 into the urethral internal wall 30. The needle 20 in contact with the bottom (guide) surface 65 of the slit 15 to guide the needle 20 so that it enters nearly perpendicular to the urethral internal wall 30. After nearly perpendicular entry, the curved needle 20 will then head in an exit direction the moment the curved needle 20 starts to penetrate the urethral internal wall 30. It is therefore possible to drive the curved needle 20 through without touching the pubic bone 27 or losing the needle 20 inside the surrounding tissue 23. After the needle 20 exits tissue 23 at 31, the surgeon will be capable of grabbing the needle tip 35 outside the urethral stump 22 and the surrounding tissue 23, leaving the suture thread 32 inside the urethral stump 22 and the surrounding tissue 23.

After a suture 66 has been placed inside the urethral stump 22 and the surrounding tissue 23 at a superior or other chosen position, an additional suture can be placed in the urethral stump 180 degrees away from the first suture in the same way the first suture was placed. Traction applied to both ends of the suture thread 32 will disengage the suture thread from the suture guide (the thread moves from the proximal portion of the slit 15 distally outwardly through the distal portion of the slit and thus exit the slit). It is now possible to turn control knob 3 to rotate suture guide 5 to the next desirable position. The suture guiding device 1 is next pushed back into the urethra 21. The slit 15 will protrude once again through the urethral stump 22. At this time, the previously placed sutures 66, will be between the urethral internal wall 30 and the suture guide 5 will be out of the way of the slit 15. Now the surgeon will be able to place additional sutures.

FIG. 3 and FIG. 4 illustrated an alternative embodiment of the suture guiding device in which the slit 15 is modified. The slit 15 in portion 13 of the suture guide 5 has a proximal portion with a wide separation or width 33 large enough to allow passage of curved needle 20, and a distal portion with a narrow separation or width 34 toward the blunt end portion 14 of the guide (i.e., adjacent the open mouth of the channel-shaped slit), allowing passage of suture thread 32 but not passage of the larger diameter curved needle 20. In this embodiment, the configuration of the slit 15 also functions as a needle pulling means, as will be described.

As shown in FIG. 3, the suture guiding device 1 with needle pulling means is inserted through the urethra 21 until the wide separation 33 can be observed as it protrudes out of the urethral stump 22. The curved needle 20 is then inserted into but not through the wide separation 33 of slit 15 to a position in which the needle tip 35 is lodged inside the narrow separation 34. As shown in FIG. 5, the suture guide 5 is then pulled back slightly into the urethra 21 (as indicated by the directional arrow 28 in FIG. 2), thereby pulling the needle 20 into the urethra 21. This action causes the curved portion 36 of the needle 20 to displace the urethral stump and the surrounding tissue 56. Retraction of the suture guiding device 1 is continued until the desired location of needle entry 29 is determined by the surgeon. The surgeon then dislodges the tip 35 of the needle 20 from the narrow separation 34 and pushes the needle through passage 33 with the needle in contact with the bottom guide surface 65 to guide the needle 20 into the urethral internal wall 30, proceeding through the surrounding tissue 23, until the curved needle 20 exits at 31. The surgeon can then grasp and pull the needle tip 35 to complete the suturing. Notice that this time the curved needle 20 does not enter perpendicularly, but at an obtuse angle 45 relative to the urethral internal wall 30, allowing the curved needle 20 to take a smaller bite 44 out of the surrounding tissue. It is important to notice that this embodiment prevents the curved needle 20 from scraping the urethral internal wall 30 when the curved needle 20 is inserted into the urethra.

FIG. 6 illustrates another embodiment of the present invention. As shown in FIG. 6, indicia 37 (e.g., an arrow) is provided on the control knob 3 to indicate the direction of the slit 15 in the guide 5. This enables the surgeon to observe the direction of the slit 15 even when the suture guide 5 is obscured by the urethra 21.

FIG. 7 depicts another embodiment of the present invention. As shown, the tubular shaft 2 includes another curved portion 38 followed by a short, straight portion 39 at the proximal end 11 of tubular shaft 2 next to control knob 3. This configuration places the axis 40 of the control knob 3 substantially parallel to the axis 41 of the suture guide 5 and allows easier manipulation of the instrument under certain circumstances.

FIG. 8 presents another embodiment of this invention. As shown in FIG. 8, the wide separation 33 and bottom guide surface 65 of the slit 15 extend obliquely in relation to the rotational axis 41 of the suture guide 5 at an acute angle 42. This slant enables the surgeon to better control the amount of bite 44 when he inserts needle 20, compare to a perpendicular angle 42.

With a perpendicular angle 42, the amount of bite 44 is determined by the surgeon, depending on the amount of protrusion of blunt end portion 14 out of the urethral stump 22. With a slant angle 42, the suture guide 5 with needle pulling means is pulled back until its blunt distal end portion 14 is flush with the urethral stump 22 and the amount of bite 44 is controlled by the angle 42.

FIG. 9 and FIG. 10 illustrate a suture guiding device 46 of our invention in which the guide and shaft are integrally formed as one piece. This suture guiding device 46 comprises a shaft of circular cross section having a straight, long section 47 with a proximal end 58, a curved section 48, and a straight, short section 49 with a blunt end 50 formed with two slits 51 lying in planes extending endwise relative to shaft section 49 at a ninety degree angular orientation relative to one another, forming a cross shape at the distal end portion 57 of the guide. Each of these slits 51 has the same function as the slit 15 of the externally controlled, rotational suture guiding device 1. In this embodiment the sutures can be placed around the urethral stump only in four places oriented at ninety degrees relative to each other. Nevertheless it has the same advantage of the externally controlled, rotational suture guiding device 1, namely allowing the curved needle 20 to enter the urethral internal wall 30 near perpendicular, thereby causing the needle 20 to head in an exit direction the moment it starts to penetrate the urethral internal wall 30.

FIGS. 10A and 10B show two different possible orientations of the cross shape (made by the two slits 51) with respect to the straight long section 47.

FIG. 11 and FIG. 12 present another embodiment of the suture guiding device 46 shown in FIG. 9 and FIG. 10.

As shown in FIG. 11 and FIG. 12, the slit has side walls which converge distally outwardly away from the bottom surface of the slit, the slit 15 thus having a proximal portion with a wide separation 52 and a distal portion with a narrow separation 53 similar to the wide separation 33 and the narrow separation 34 of slit 15 of the externally controlled, rotational suture guiding device 1 described previously. This embodiment also incorporates the aforementioned needle pulling means.

Figure 13:
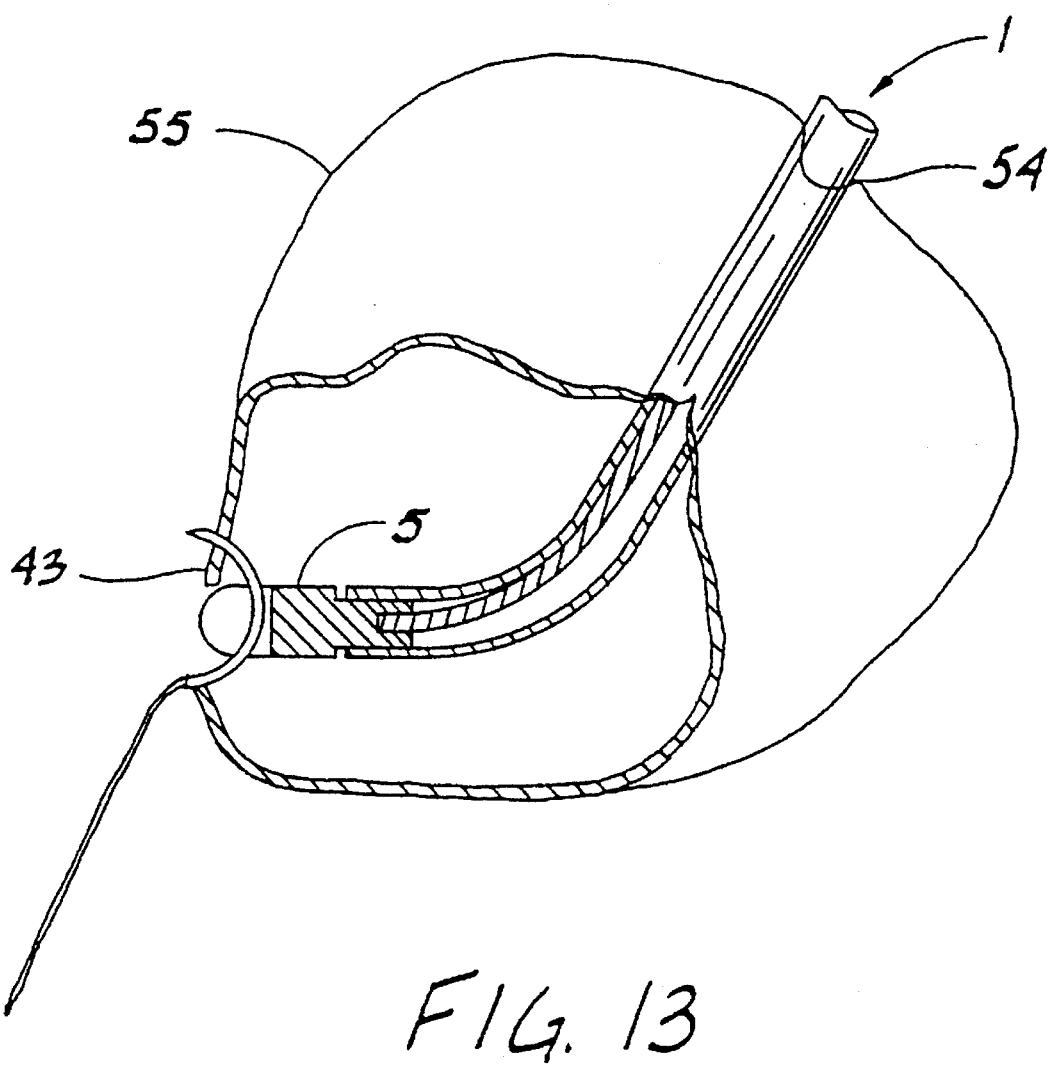
FIG. 13 illustrates a procedure for another usage of the device in FIG. 1, FIG. 9 and FIG. 11.
Figure 24:
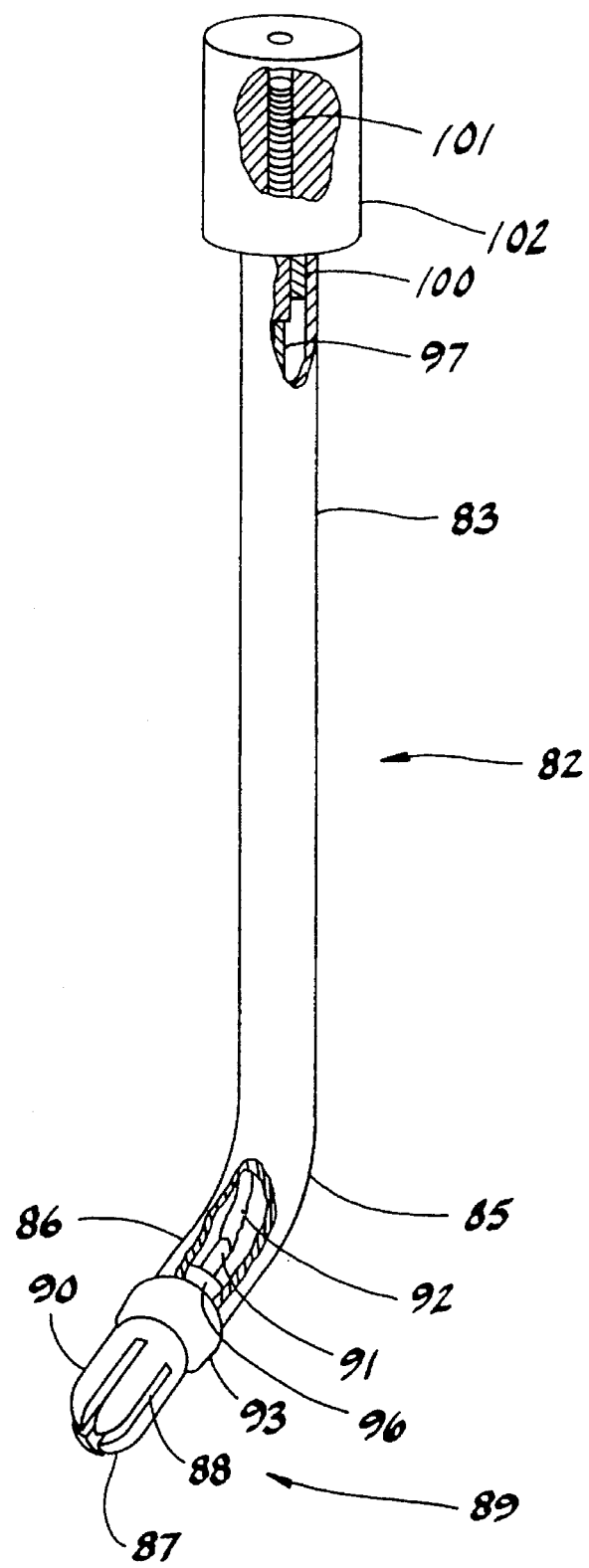
FIG. 24 is an isometric view of the instrument shown in FIG. 21.

FIG. 13 presents another procedure for the usage of the externally controlled, rotational suture guiding device 1 incorporating a slit configured to pull a needle as described heretofore. In this procedure, the device is inserted through a cystotomy 54 in the bladder wall 55, allowing the suture guide 5 to exit through the bladder neck 43 during bladder reconstruction in order to assist the guiding of the suture to the bladder neck during anastomosis of the bladder to the urethral stump.

FIG. 14 and FIG. 15 present another instrument 59 of the present invention. As shown in FIG. 14, a suture guide 5 is provided at each end of the instrument creating a reversible, externally controlled, rotational suture guiding device with needle pulling means. This embodiment allows the surgeon to insert either end of this device first, giving the surgeon the choice between two different suture guides 5. For example, the slit(s) in one guide 5 may have parallel walls, and the slit in the other guide 5 may have converging side walls to provide for aforementioned needle pulling means.

FIG. 15 is a sectional view of a guide 5 shown in FIG. 14. This view illustrates how to assemble the instrument. Before assembling the instrument, the parts have to be made in a sequential order. One of the suture guides 5 is constructed with a hole 26 going through the entire length of the guide 5 but the slit 15 is not cut at this time. The other suture guide 5 is constructed with a partial hole 26 and with a slit 15. Then the tubular shaft 2 is bent to shape. To assemble the unit, join the suture guide 5 that has the slit, to the flexible shaft 4 in the same way that it is done for the instrument if FIG. 1 (bonded or brazed). The flexible shaft 4 is then inserted through the tubular shaft 2. Flexible shaft 4 is then inserted inside hole 26 of the other suture guide 5 (the one without a slit 15) and guide 5 is then slid up the flexible shaft 4 until suture guide 5 is inserted securely inside the short, straight tubular portion 6. By pulling flexible shaft 4 firmly while holding suture guide 5 (the one without the slit), the suture guide 5 at both ends of the suture guiding device 60 will be properly positioned inside respective ends 57 of the tubular shaft 2. Then the components of the suture guiding device 60 are held together by tightening set screw 61 against flexible shaft 4. After the instrument is an integral unit, a spot weld 62 at the head of the set screw 61 can be added and the excess ground smooth. This is done to prevent the set screw from backing up. Now it is possible to cut the slit 15 and to eliminate the excess of flexible shaft 4.

FIG. 16 presents another embodiment of the present invention. As it can be observed, suture guiding device 60 is of one piece construction and has suture guides 5 at both ends, like suture guiding device 46, thus creating a reversible device with needle pulling means. This embodiment also allows the surgeon to select either of two different suture guides, such as two guides having different diameters or slit configurations.

FIG. 17 presents another embodiment of the present invention. The instrument 63 in FIG. 17 is a flexible, externally controlled, rotational suture guiding device. This instrument 63 is similar to the externally controlled, rotational suture guiding device of FIG. 1, except it includes a flexible tubular shaft instead of a rigid tubular shaft. This instrument is comprised of a tubular shaft 64, having opposite ends which are distal 57 and proximal 58 relative to a person holding the device for use in a suturing procedure, the distal end 57 of the shaft being adapted to be inserted into a patient during the procedure. The device also includes a suture guide 5 mounted at the distal end 57 of the flexible tubular shaft 64 for rotation relative to the flexible tubular shaft 64 about an axis extending endwise with respect to the flexible tubular shaft 64, a control knob 3 at the proximal end 58 of the shaft and a flexible shaft 4 (not shown) inside the tubular shaft 64 interconnecting the suture guide portion 5 and the control knob 3. This instrument is especially suited for anastomosing two tubular structures during laparoscopic surgery.

Referring now to the embodiments of the suturing instrument for impeding the flow of blood around a suturing site of the present invention, such suturing instruments comprise a substantially rigid shaft having opposite ends which are distal and proximal relative to a person holding the instrument, the distal end of the shaft being adapted to be inserted into a patient during said procedure, an expansible annular member of flexible, resilient material encircling the shaft adjacent its distal end, and expansion means for expanding said annular member radially outwardly relative to the shaft to impede the flow of blood around a suturing site. Several embodiments of the suturing instrument with hemorrhaging control are shown in the Figures and explained in detail below.

FIGS. 18–20 illustrate one embodiment of the suturing instrument for impeding the flow of blood around a suturing site, generally indicated at 68. In this embodiment, the suturing instrument 68 is an assembly made up of two components; the suture guiding device and a balloon assembly. The balloon assembly includes an expansible annular member 80 of flexible, resilient material encircling the shaft adjacent its distal end, an elongate tube 81 and an inflation device 107.

As shown in FIGS. 18–20, suture guiding device 68 comprises a rigid, preferably bent shaft 69 of circular cross section having a proximal end, generally indicated at 72, and a distal end, generally indicated at 77. The distal end 77 of the shaft is adapted to be inserted into a patient during the suturing procedure. The shaft includes a long straight section 71, a curved section 73, and a short straight section 74 with a blunt distal end 75. The blunt end 75 is formed with two slits, each designated 76, lying in planes extending endwise relative to short section 74 at a ninety degree angular orientation relative to one another to form a cross shape at the distal end 77 of the guide. Each slit 76 has the same function as the slit 15 of applicant's externally controlled, rotational suture guiding device shown in FIG. 1 and disclosed in co-pending patent application Ser. No. 07/992,494 now U.S. Pat. No. 5,342,374. In this embodiment, the sutures can be placed around the urethral stump only in four places oriented at ninety degrees relative to each other. Nevertheless, it has the same advantage of the externally controlled, rotational suture guiding device, specifically allowing the curved needle 20 (FIG. 38) to enter the urethral internal wall 30 near perpendicular. This causes the needle to head in an exit direction the moment it starts to penetrate the urethral internal wall 30.

In addition, suture guiding device 69, incorporates an annular channel (or groove) 78 around the perimeter of short section 74 and a longitudinal groove 79 which extends along the side of the straight section 71 from the annular channel 78 to the proximal end 72 of the shaft.

Expansible member 80 is made up of a hollow member generally toroidal in shape having an inlet 80A. Expansion means for expanding the hollow annular member 80 radially outwardly relative to the shaft comprises the tube 81 and inflation device 107 of the balloon assembly. Expansible member 80 is made of a resilient material and is capable of being slipped over blunt end 75 and removably seated in annular channel 78. Thus, expansible member 80 can be removed to allow the user to replace the member from the suture guiding device 68 after every suturing procedure. A conduit in the form of an elongate tube 81 is attached at its distal end to inlet 80A of the expansible member 80 and is disposed in the entire length of longitudinal groove 79. Inflation device 107 comprises an inflator 107A, such as a pump, syringe or other pressurized source of fluid, and a release valve (not shown). The release valve is conventional in the balloon inflation field (e.g., the same valve is used on the balloon device of a Foley catheter). Preferably, the release valve is adapted so that the inflator 107A releasably connects to a cooperating fitting (not shown) on the valve. The inflation device 107 is attached to the proximal end of the tube 81 and the inflator 107A supplies fluid 106— preferably water—under pressure into elongate tube 81 which conveys the fluid into expansible member 80 and expands it. The release valve allows the deflation of the expansible member 80 when so desired by the user. The tube 81 and expansible member 80 are preferably of a one-piece construction.

Figure 37:
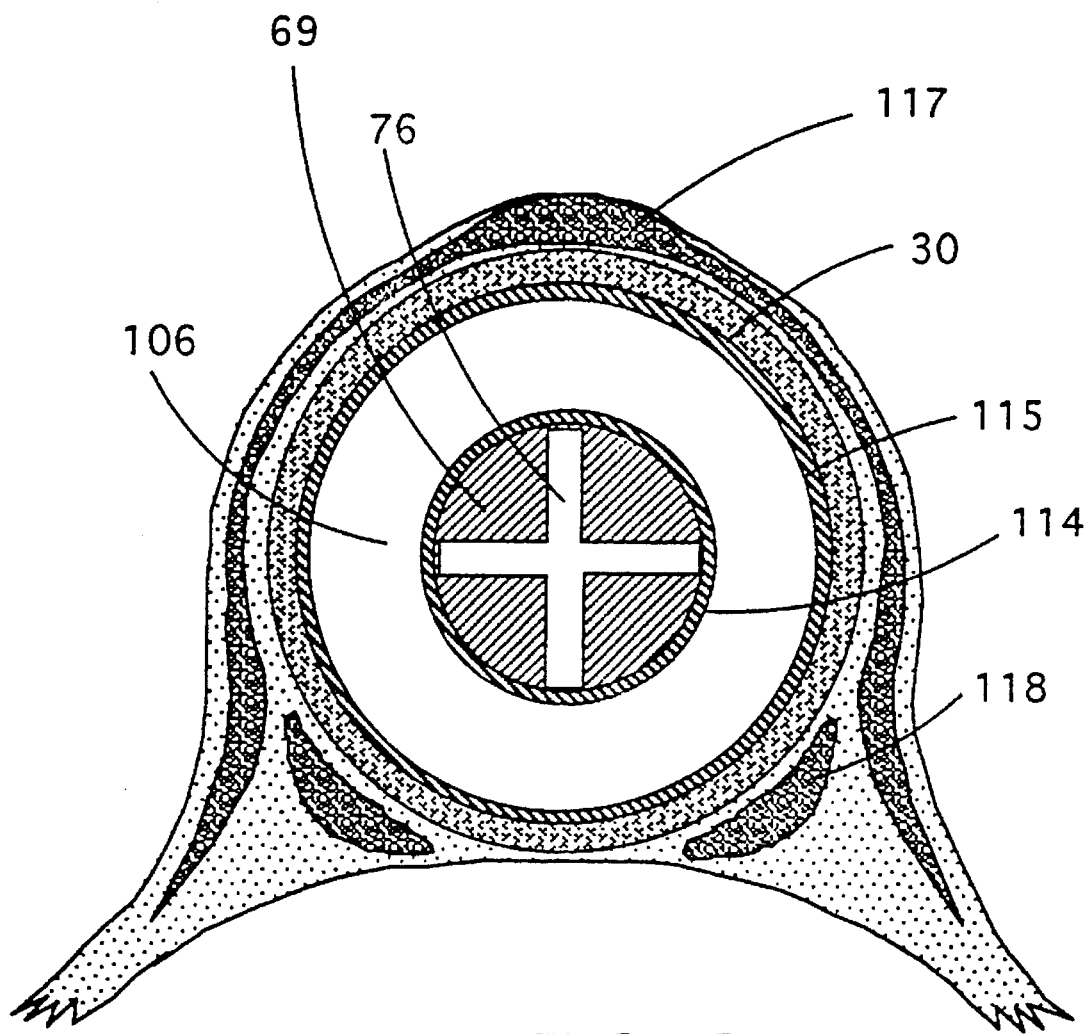
FIG. 37 is a sectional view taken along line 37—37 of FIG. 36 showing the suturing instrument with hemorrhaging control shown inside the urethra after inflation.
Figure 38:
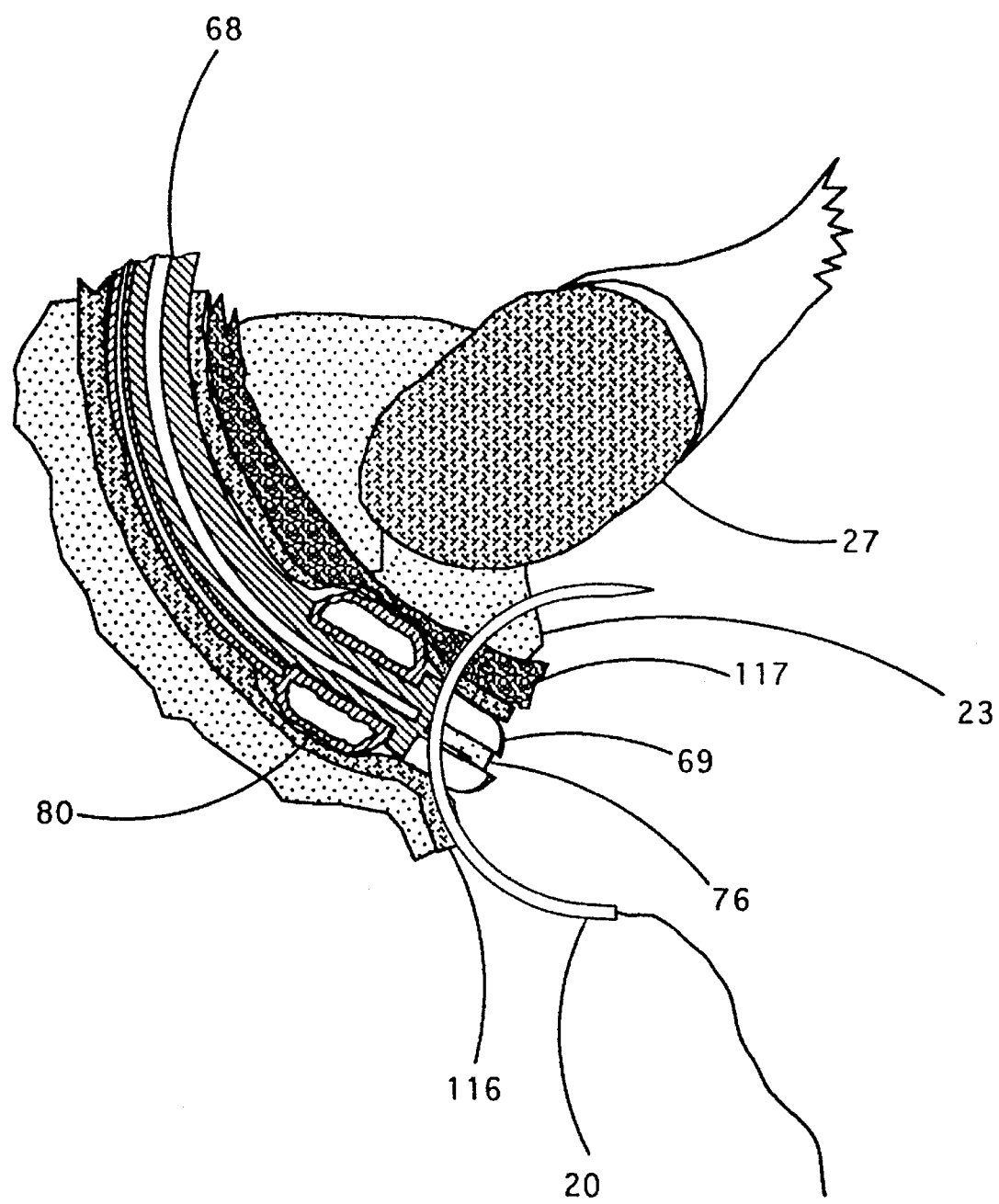
FIG. 38 is the same view as FIG. 34 showing the suturing instrument with hemorrhaging control inside the urethra while the suture is being guided.

As shown in FIGS. 34–37, when the expansible member 80 expands, its inner wall 114 presses against the suture guiding device 69 and its outer wall 115 presses against the urethral internal wall 30 (FIG. 37). The pressure of the expansible member 80 against the total perimeter of the urethral internal wall 30 will also provide pressure to the dorsal vein complex 117 and the lateral vascular bundle 118. This pressure serves to substantially diminish the hemorrhaging of the severed dorsal vein complex and the bleeding of the urethral stump 116 during suturing procedure. As shown in FIG. 38, a secondary use of this internal pressure is to keep the suture guiding device 68 from slipping through the urethral internal wall 30. As the surgeon pushes the suture guiding device 68 (with the expansible member expanded) deeper into the pelvis, the suture guiding device 68 will cause eversion of the urethral stump, carrying the urethral stump 116 away from the surrounding tissue 23. Exposing the urethral stump 116 will provide the surgeon a better view so that sutures can be placed in the most desired locations.

A second embodiment of the suturing instrument for impeding the flow of blood around a suturing site is shown in FIGS. 21–24. In this embodiment, the suturing instrument 82 comprises a rigid, preferably bent shaft of a circular, hollow cross section having a straight, long section 83 with a proximal end 84, a curved section 85, and a straight, short section 86 with a blunt end 87. The blunt end is formed with two slits, each designated 88, lying in planes extending endwise relative to short section 86 at a ninety degree angular orientation relative to one another to form a cross shape at a distal end 89 of the suturing instrument. Each slit 88 has the same function as the slit 15 of the externally controlled, rotational suture guiding device of applicant's above-referenced co-pending application shown in FIG. 1.

In this embodiment the sutures can be placed around the urethral stump only in four places oriented at ninety degrees relative to each other. Nevertheless, it has the same advantage of the externally controlled, rotational suture guiding device, namely allowing the curved needle 20 to enter the urethral internal wall 30 near perpendicular, thereby causing the needle 20 to head in an exit direction the moment it starts to penetrate the urethral internal wall 30.

Blunt end 87 and the two slits 88 are part of a retractable head 90 extending axially with respect to distal end 89 of the tubular shaft. The retractable head 90 has a distal end portion (the blunt end) 87 and a proximal end portion 91, the proximal end portion of the head having a diameter smaller than that of the distal end portion of the head. The smaller diameter proximal end portion 91 has a resilient expansible tubular member or sleeve 93 mounted loosely around it. This resilient member 93 is capable of being squeezed between the shoulder 94 of the retractable head 90 and the end surface 95 of a tubular guide 96. Tubular guide 96 is capable of guiding axially the smaller diameter proximal end portion 91 of the retractable head 90. Tubular guide 96 is installed tightly inside the straight, short section 86 of the shaft at its distal end 89. Proximal end portion 91 of the retractable head is attached to a cable 92. The other end of cable 92 is attached to a threaded member 97 which is in threadable engagement with a control knob 102. Attached firmly to the threaded member 97 is a guiding key 98 to keep threaded member 97 from spinning inside a bushing 100. Guiding key 98 is capable of sliding along groove 99. Groove 99 is located axially inside bushing 100. Bushing 100 is attached firmly inside the straight, long section 83 at proximal end 84 of the shaft. Threaded member 97 has threads 101 on which a control knob 102 is threadably installed. The cable, threaded member, and control knob comprise part of the expansion means in this embodiment of the present invention.

After the suturing instrument 82 is inserted into the patient during the procedure, blunt end 87 is allowed to protrude out of the urethral stump 116. Control knob 102 is then turned to force threaded member 97 to move longitudinally away 104 from the suturing instrument 82 and forcing face 103 of control knob 102 to push against face 105 of bushing 100. As the threaded member 97 is moving away 104 from suturing instrument 82, threaded member 97 pulls cable 92 and cable 92, in turn, pulls smaller diameter proximal end portion 91. This forces the retractable head 90 to squeeze the expansible, resilient member 93 between a face 94 of retractable head 90 and a face 95 of tubular guide 96, respectively. Squeezing the expansible, resilient member 93 causes it to bulge in a generally radially outward direction. When expansible member 93 bulges outward, it presses against the entire perimeter of the urethral internal wall 30. The pressure of the expansible member 93 against the perimeter of the urethral internal wall 30 will also provide pressure to the dorsal vein complex 117 and the lateral vascular bundle 118. This pressure helps to stop hemorrhaging of the severed dorsal vein complex and the bleeding of the urethral stump 116 during suturing procedure. A secondary use of this internal pressure is to keep the suturing instrument 82 from slipping through the urethral internal wall 30. As the surgeon pushes the suture guiding device 82 deeper into the pelvis, the suturing instrument 82 will carry the urethral stump 116 away from the surrounding tissue 23. Exposing the urethral stump 116 will provide the surgeon a better view so that sutures can be placed in the most desired locations.

A third embodiment of the suturing instrument for impeding the flow of blood around a suturing site is shown in FIGS. 25–27. As shown in these views, suture guiding device 112 is the same instrument as illustrated in FIGS. 18–20 except that it further includes a longitudinal passageway 108 extending through the shaft of the suture guiding device 113 from its proximal end to its distal end for insertion of medical implements therethrough. This is accomplished by starting the manufacturing of the shaft of the suture guiding device with a tube having a large wall thickness and a small hole. The longitudinal passageway 108 of this embodiment is included for the purpose of passage of a guiding wire to help guide the suturing instrument in some special bladder operations and, alternatively, for inserting fiber optics when desired.

Figure 39:
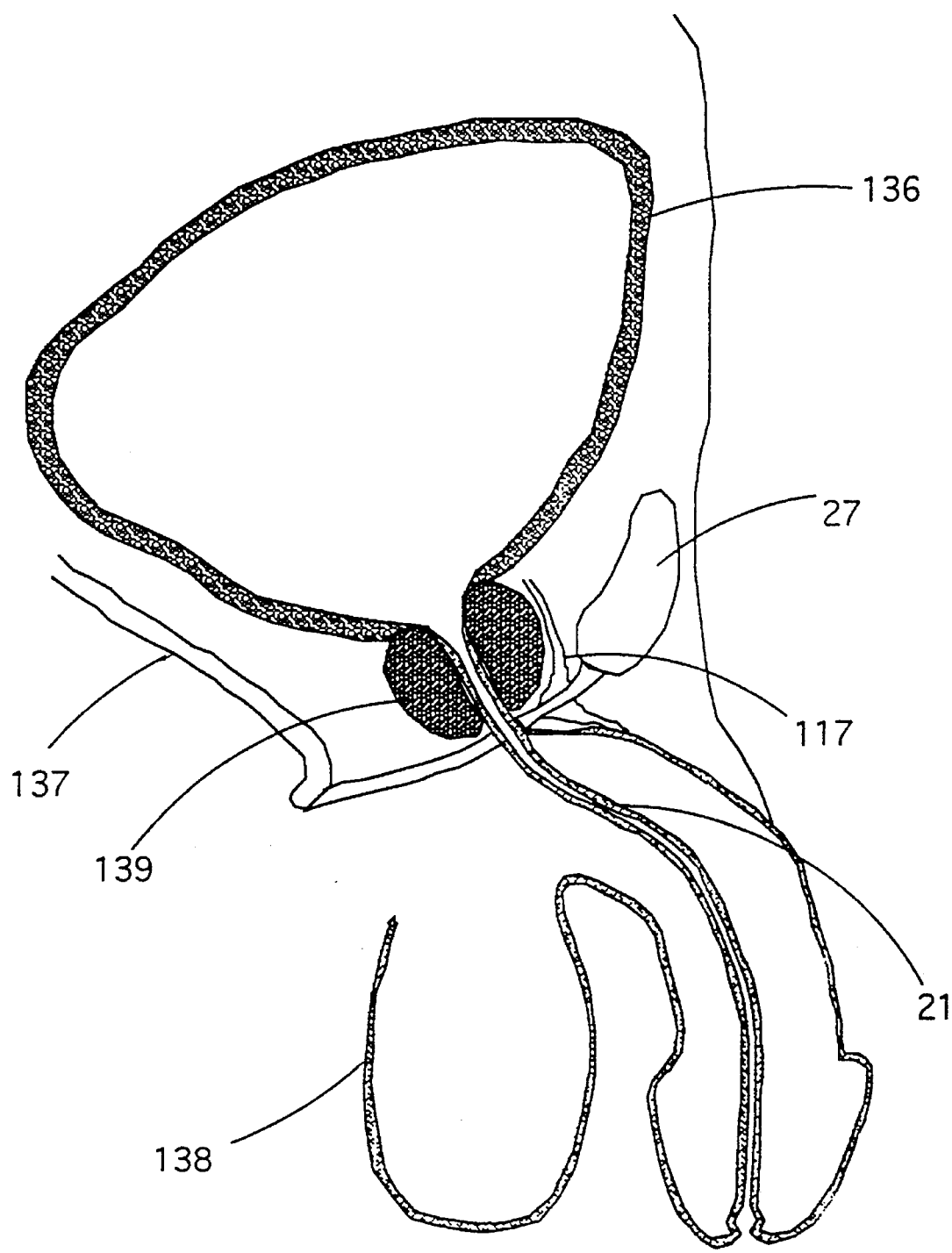
FIG. 39 is a sectional view showing a normal male anatomy.
Figure 40:
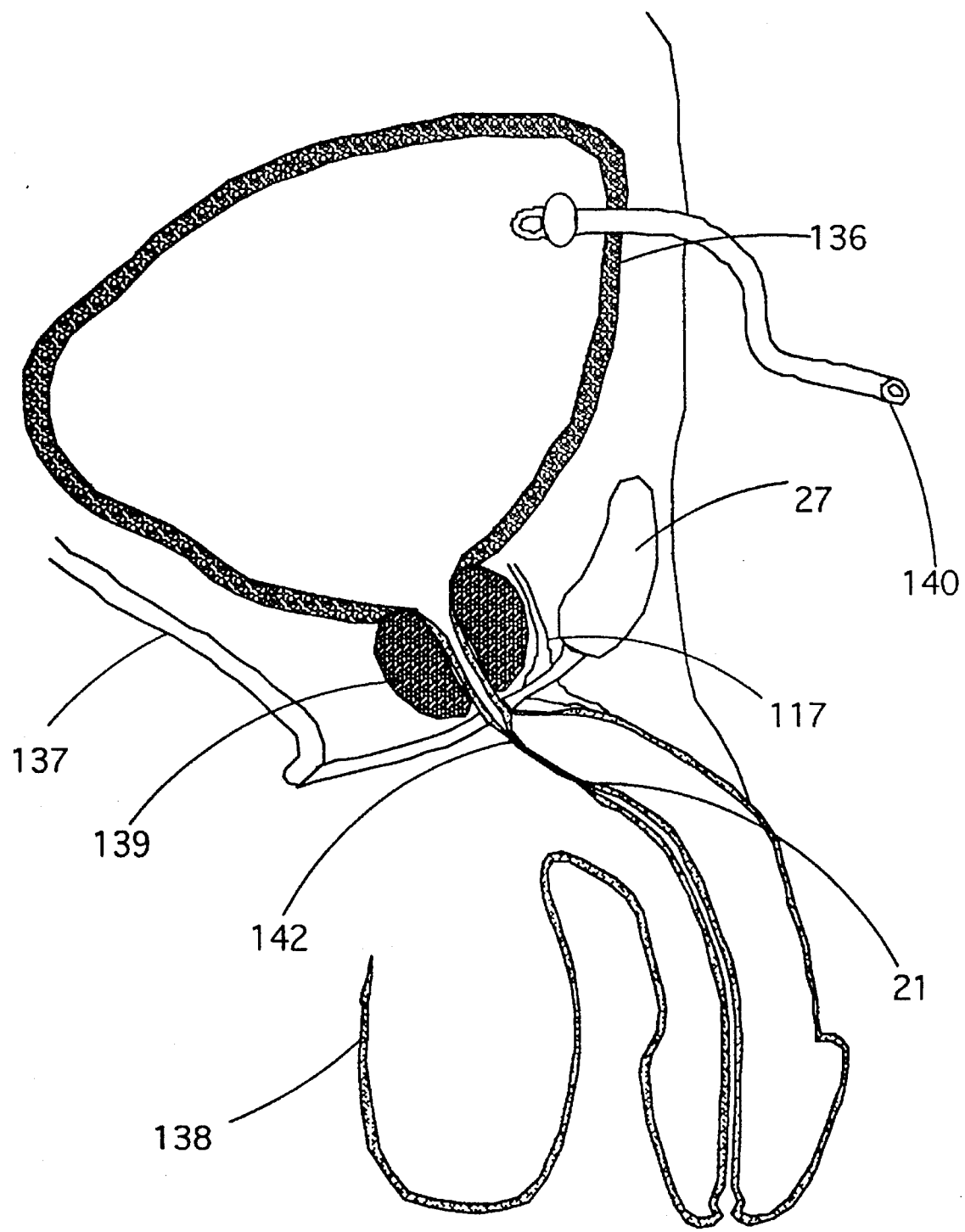
FIG. 40 is a sectional view showing the male anatomy following a membranous urethral disruption.
Figure 41:
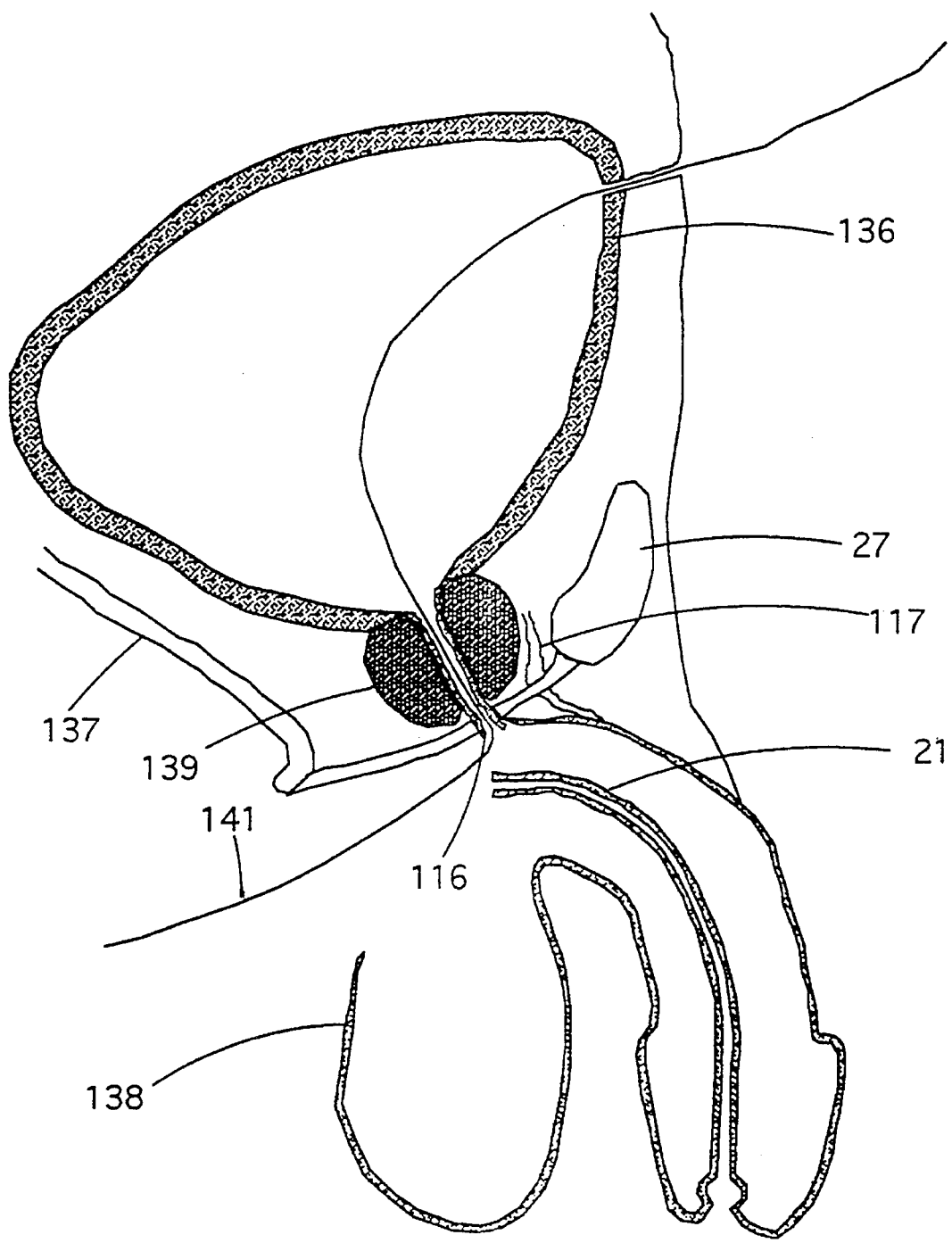
FIG. 41 is a sectional view showing the male anatomy after the urethra has been separated from the prostate and a wire has been passed through suprapubic cystostomy tract and is allowed to protrude out of the prostatic urethral stump.
Figure 42:
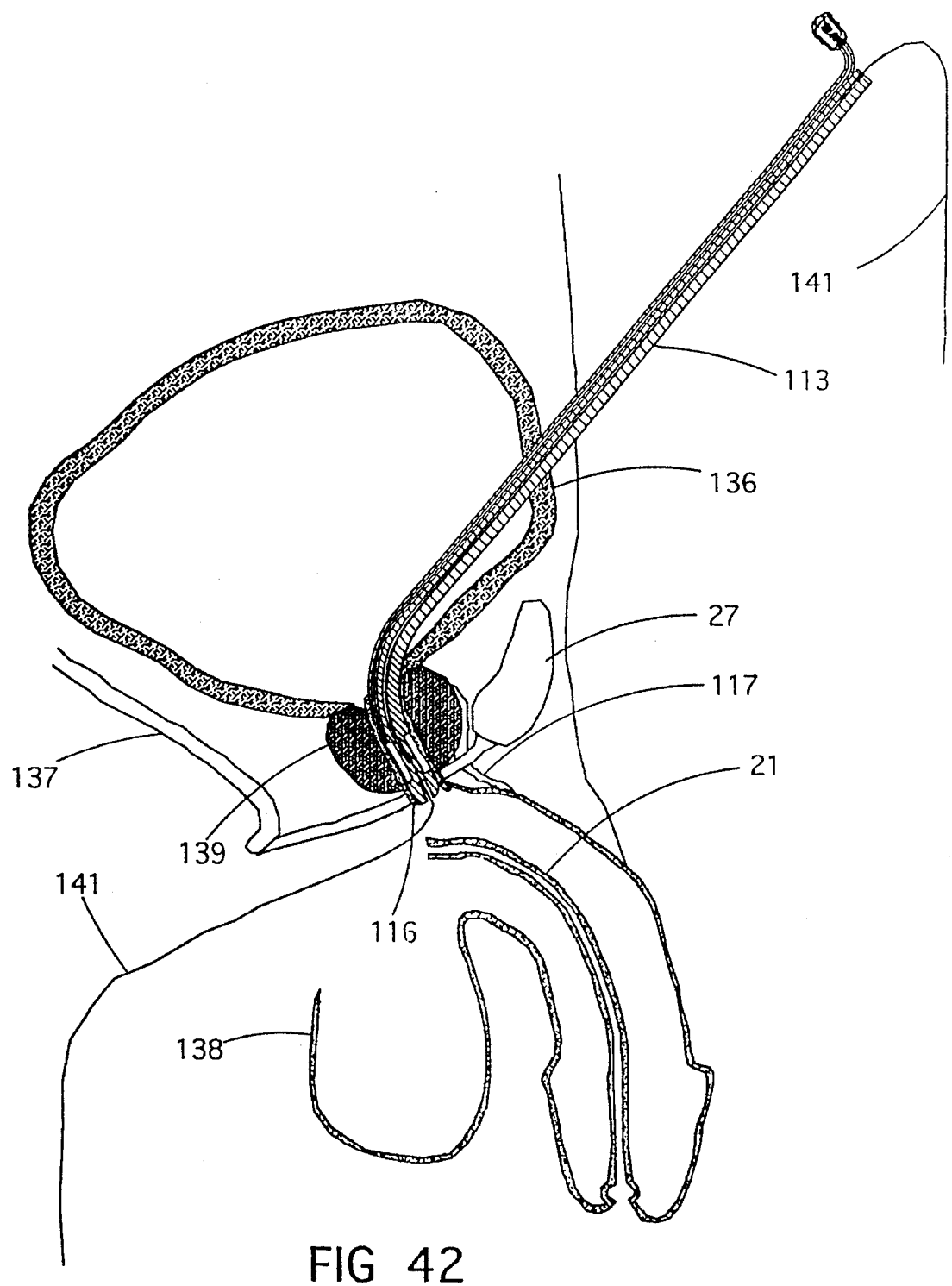
FIG. 42 is a sectional view showing the suturing instrument as it is passed through suprapubic cystostomy tract over the guide wire.
Figure 43:
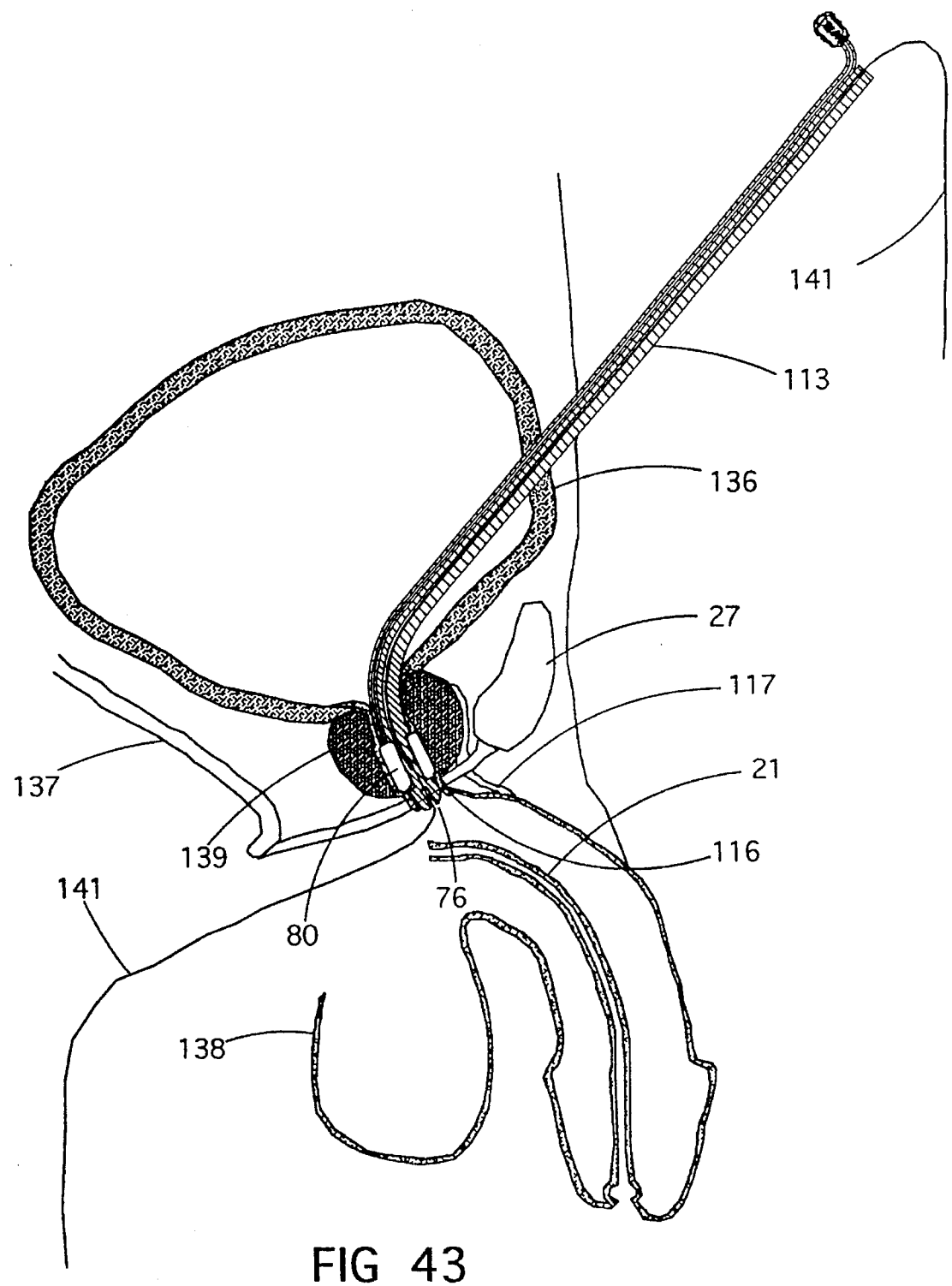
FIG. 43 is a sectional view showing the suturing instrument as an expansible member is expanded to compress the urethral stump for hemostasis.
Figure 46:
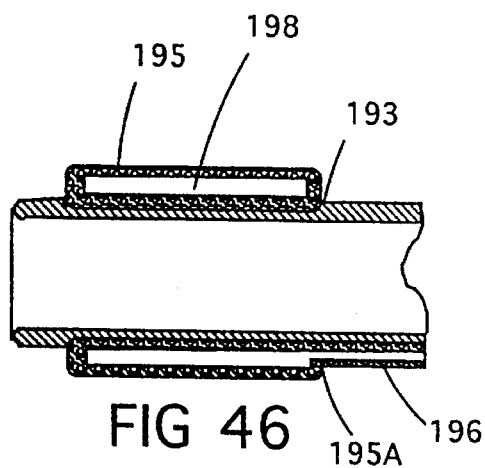
FIG. 46 is a partial view of the instrument shown in FIG. 44, after inflation of the expansible member.
Figure 45:
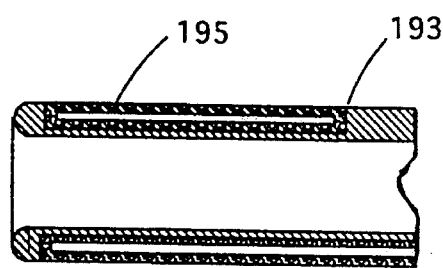
FIG. 45 is a partial view of the instrument shown in FIG. 44 prior to inflation of an expansible member.
Figure 44:
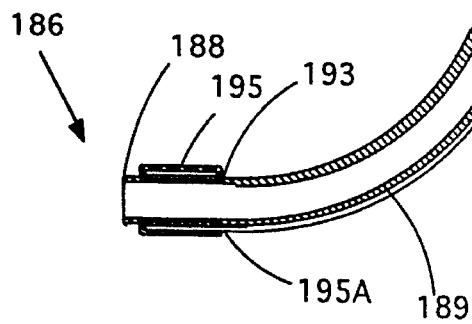
FIG. 44 is a vertical sectional view of another embodiment of the suturing instrument with hemorrhaging control of the present invention.
Figure 47:
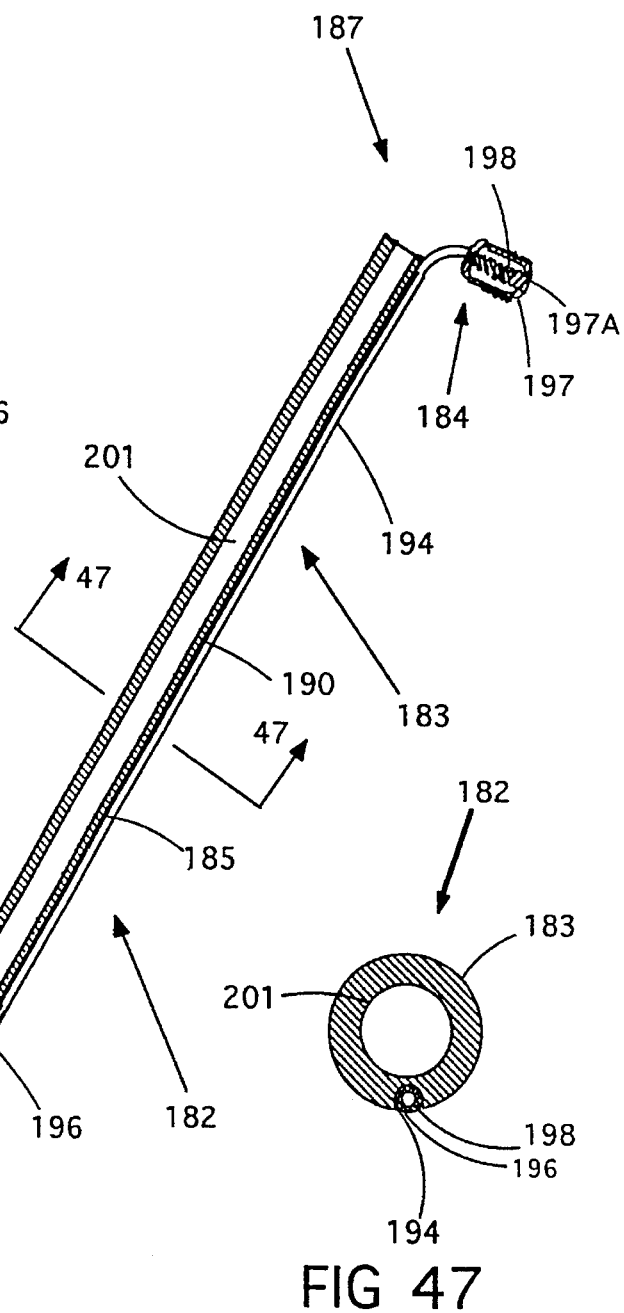
FIG. 47 is a sectional view taken along line 47—47 of FIG. 44.

This embodiment is used for transperineal repair of membranous urethral disruption as shown in FIGS. 39–43. FIG. 39 presents a normal male anatomy. FIG. 40 presents the male anatomy following a membranous urethral disruption. As it can be observed, when the urethra 21 has been damaged, indwelling suprapubic cystostomy catheter 140 into bladder 136 will allow urine evacuation. This is normally done to allow stricture 142 of urethra 21 to be formed. After the stricture 142 of urethra has been formed, the urethra 21 is separated from the prostate 139 and a wire 141 is passed through suprapubic cystostomy tract and is allowed to protrude out of prostatic urethral stump 116 as shown in FIG. 41. As shown in FIG. 42, the suturing instrument 113 is passed through suprapubic cystostomy tract over guide wire 141. The blunt end 75 is allowed to protrude a few millimeters out of prostatic urethral stump 116. The expansible member 80 is now expanded to compress the urethral stump for hemostasis and to cause eversion of the urethral stump as the suture guiding device 113 is advanced distally as shown in FIG. 43. Sutures can now be placed in desirable location and depth through the slit 76.

Figures 28, 29, 30:
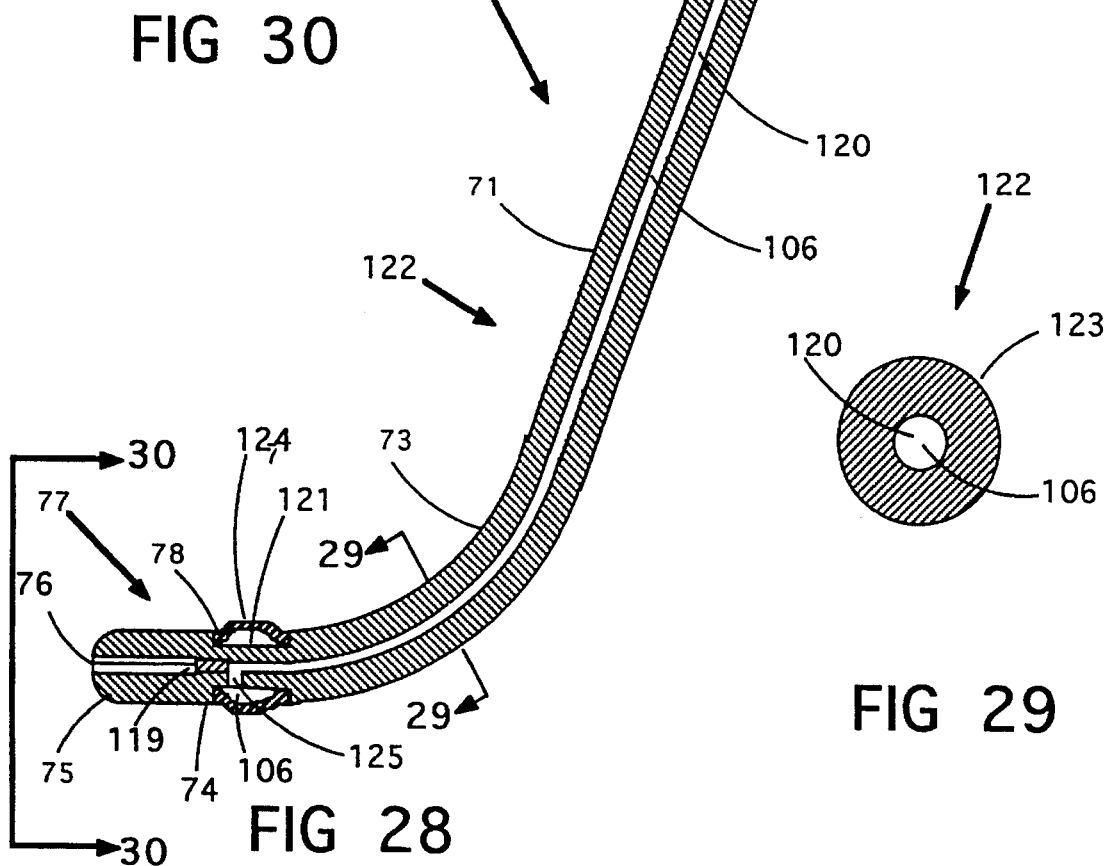
FIG. 28 is a vertical section of another embodiment of a suturing instrument with hemorrhaging control of the present invention.
FIG. 29 is a sectional view taken along line 29—29 of FIG. 28.
FIG. 30 is partial end view of the instrument shown in FIG. 28.
Figure 34:
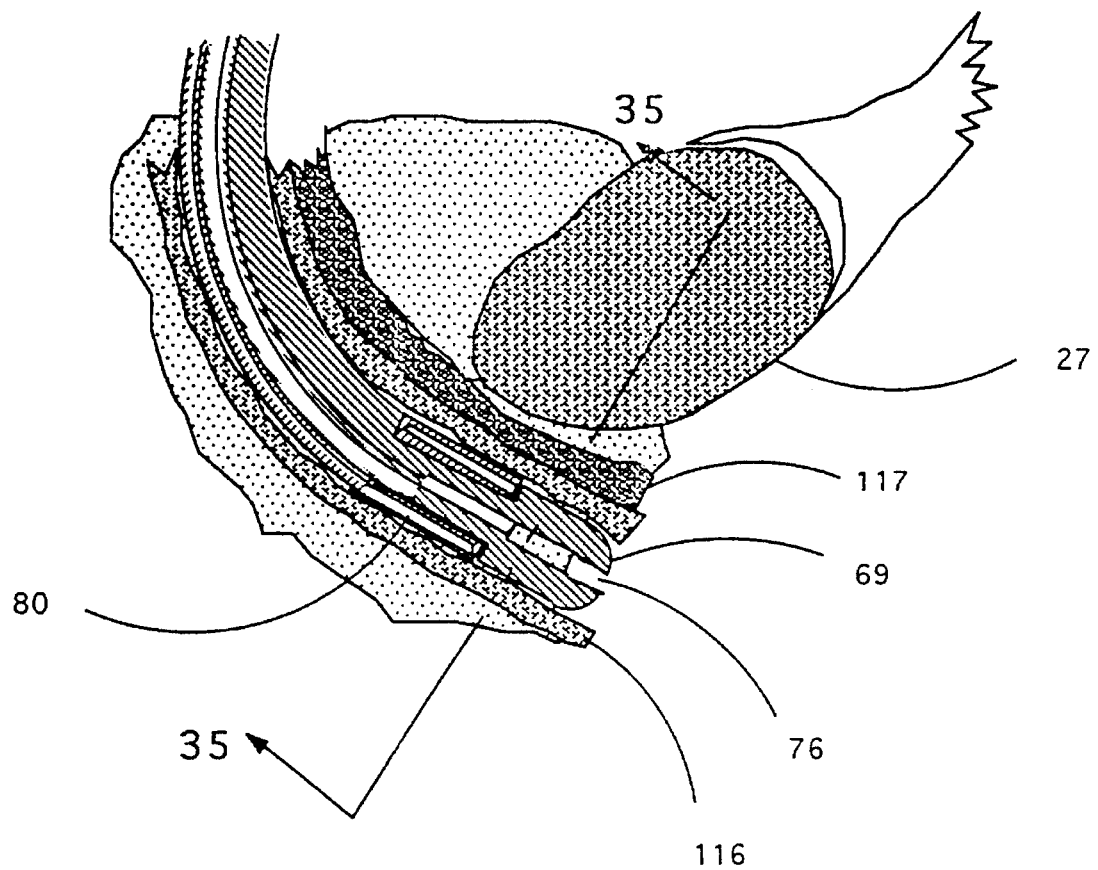
FIG. 34 is a partial cross section of a suturing instrument with hemorrhaging control shown inside the urethra prior to inflation.
Figure 35:
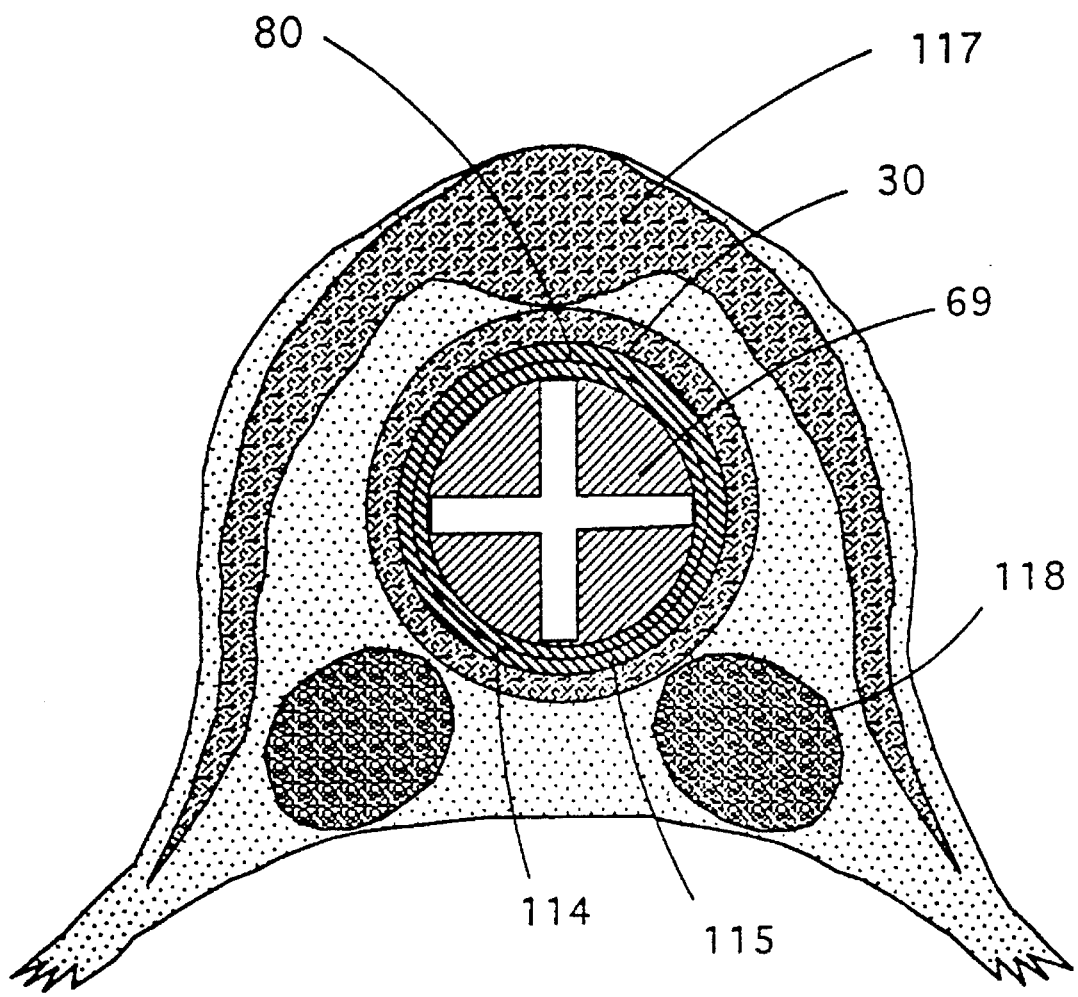
FIG. 35 is a sectional view taken along line 35—35 of FIG. 34.
Figure 36:
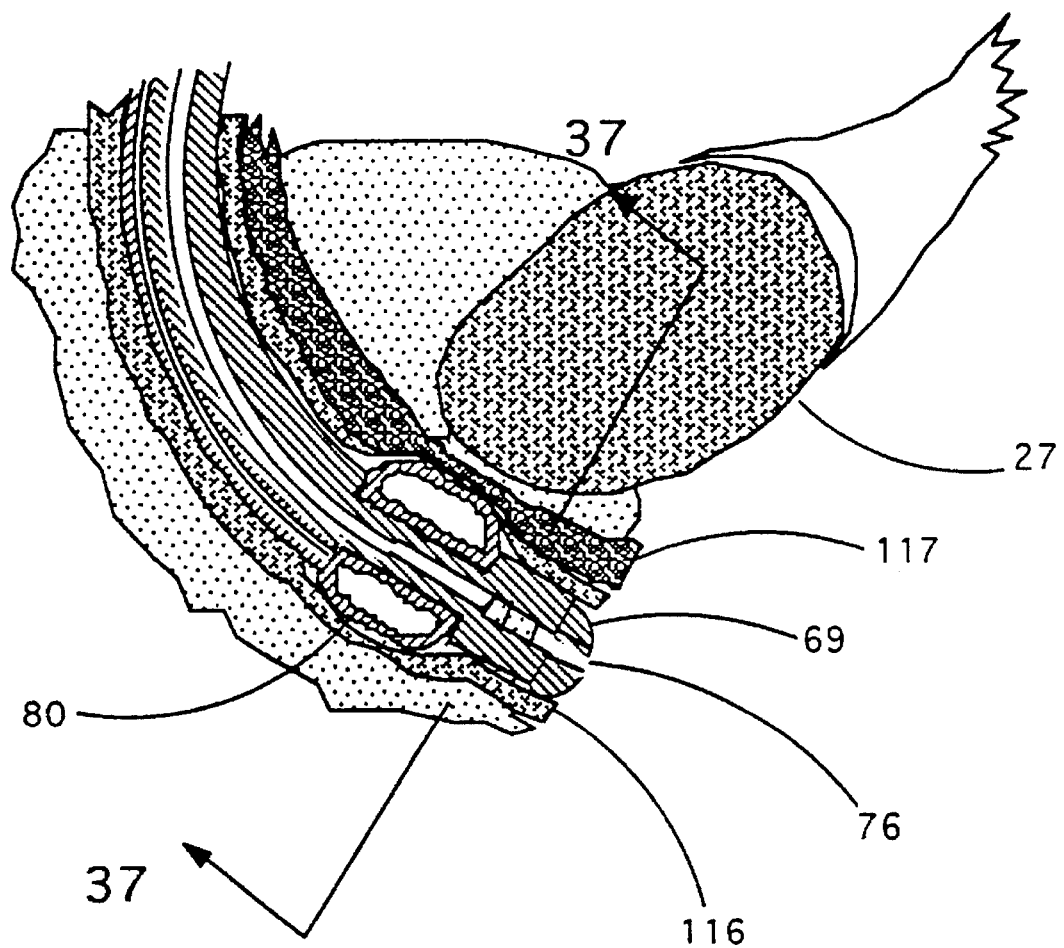
FIG. 36 is the same view as FIG. 34 showing the suturing instrument with hemorrhaging control shown inside the urethra after inflation.

FIGS. 28–30 illustrate views of another embodiment of the suturing instrument for impeding the flow of blood around a suturing site of the present invention. In this embodiment, the suturing instrument 122 is an assembly made up of three components; a suture guiding device 123, an expansible member 124 and an inflation device 107.

Suture guiding device 123 comprises a rigid, preferably bent shaft of circular tubular cross section with a longitudinal passageway 120, the shaft having a proximal end, generally indicated at 72, and a distal end, generally indicated at 77. The distal end 77 of the shaft is adapted to be inserted into a patient during the suturing procedure. The shaft includes a straight, long section 71, a curved section 73, and a straight, short section 74, with a blunt end 75 formed with two slits, each designated at 76. The slits 76 lie in planes extending endwise relative to short section 74 at a ninety degree angular orientation relative to one another to form a cross shape at the distal end 77 of the suture guiding device. Each slit 76 has the same function as the slit 15 of the externally controlled, rotational suture guiding device of applicant's co-pending application, shown in FIG. 1. In this embodiment, the sutures can be placed around the urethral stump only in four places, oriented at ninety degrees relative to each other. Nevertheless, it has the same advantage as applicant's externally controlled, rotational suture guiding device, specifically allowing the curved needle 20 to enter the urethral internal wall 30 near perpendicularly (FIG. 38). This causes the needle 20 to head in an exit direction the moment it starts to penetrate the urethral internal wall 30. In addition, suture guiding device 123, incorporates an annular channel 78 around the perimeter of short section 74. A second passageway 125 interconnects the longitudinal passageway 120 and the channel 78. This second passageway 125 allows fluid 106 to get inside a cavity 121 formed by channel 78 and expansible member 124 which encircles the channel.

Expansible member 124 is made of a resilient material and is attached firmly over blunt end 75 inside groove 78. An inflation device 107 for expanding the expansible member is attached to the proximal end 72 of the suture guiding device 122. This inflation device 107 is the same as the inflation device described in the embodiment of the present invention shown in FIGS. 18–21. The inflation device supplies fluid 106 under pressure to the cavity 121 and further allows the evacuation of fluid 106 from inside the cavity 121 when so desired by the user. Fluid 106 is forced under pressure by inflator 107A into longitudinal passageway 120 which guides fluid 106 through second passageway 125 and into cavity 121 to expand expansible member 124. The release valve (not shown) allows deflation of the expansible member 124 when desired by the user. The inflation device and the passageways comprise the expansion means. When member 124 expands, it presses against the perimeter of the urethral internal wall 30. The pressure of the expansible member 124 against the total perimeter of the urethral internal wall 30 will also provide pressure to the dorsal vein complex 117 and the lateral vascular bundle 118. This pressure helps to stop the hemorrhaging of a severed urethra and also the bleeding of the urethra stump 116 during suturing procedures. A secondary use of this internal pressure is to keep the suture guiding device 123 from slipping through the urethral internal wall 30. As the surgeon pushes the suturing instrument 123 with the expansible member expanded deeper into the urethral meatus, the suture guiding device 123 will carry the urethral stump 116 away from the surrounding tissue 23. Exposing the urethral stump 116 will provide the surgeon a better view so that sutures can be placed in the most desired locations.

FIGS. 31–33 illustrate views of another embodiment of the suturing instrument for impeding the flow of blood around a suturing site in which the suturing instrument 128 is an assembly made up of a suture guiding device 127 and a balloon assembly.

Suture guiding device 127 comprises a rigid, preferably bent shaft 130 having opposite ends which are distal 77 and proximal 72 relative to a person holding the device for use in a suturing procedure, the distal end 77 of the shaft being adapted to be inserted into a patient during the procedure. The device 127 further comprises a suture guide 5 mounted at the distal end 77 of the shaft 130 for rotation relative to the shaft 130 about an axis extending endwise with respect to the tubular shaft 130, a control knob 3 at the proximal end 72 and means comprising a flexible shaft 4 interconnecting the suture guide 5 and the control knob 3. The rigid shaft 130 has a short, straight distal section 131, followed by a curved section 132, followed by a long, straight section 133. When the suture guiding device 127 is in use, the shaft 130 must be capable of being manually grasped at the long, straight section 133, and kept in control by the surgeon while inserted into the urethral meatus and guided all the way through the urethra 21 to eventually protrude out of the urethral stump 116 in the same manner as a standard urethral sound is used.

The control knob 3 consists of a member 9 with a counterbore 10 and a small diameter hole 25. The counterbore 10 has to be capable of spinning around end 11 of tubular shaft 130. The counterbore 10 has to be deep enough to support and stabilize control knob 3 on end 11 of tubular shaft 130. The small hole 25 is the portion of the control knob 3 that accepts and holds flexible shaft 4. Suture guide 5 is an elongate member extending axially with respect to the straight tubular distal section 131 of the tubular shaft 130. The guide 5 has a smaller diameter proximal end portion 12 with a small hole 26 extending axially of the guide, a larger diameter middle portion 13, and a blunt distal end portion 14. A slit 15 is formed in the blunt end portion 14 and extends into the larger diameter middle portion 13. The slit 15 is wide enough to allow passage of a curved needle 20 through the blunt end portion 14 and into the middle shaft portion 13. The slit 15 has generally parallel side walls and a bottom surface or floor 65 which extends generally perpendicular to the longitudinal axis of the guide 5. End 24 of flexible shaft 4 is attached at 18 firmly inside hole 25 of control knob 3. The shaft 4 extends through the tubular shaft 130 and is attached at 19 firmly inside hole 26 of suture guide 5. Small diameter proximal end portion 12 of suture guide 5 is capable of spinning inside hole 129 of the short straight tubular distal section 131 of tubular shaft 130. The proximal end portion 12 of suture guide 5 must be long enough to support and stabilize itself inside hole 129 of tubular shaft 130. As it can be seen, when control knob 3 is manually rotated, the flexible shaft 4 is capable of transmitting the rotation to the suture guide 5. This rotation allows the slit 15 in the guide to be oriented at any location around the urethral stump 22 during a radical prostatectomy procedure or tubular anastomosis. Slits 15 have the same function as the slit of the externally controlled, rotational suture guiding device of applicant's co-pending application shown in FIG. 1. Suture guiding device 127 has the same advantage of applicant's externally controlled, rotational suture guiding device specifically allowing the curved needle 20 to enter the urethral internal wall 30 near perpendicular (FIG. 38). This causes the needle 20 to head in an exit direction the moment it starts to penetrate the urethral internal wall 30. In addition, the shaft 130 of the suture guiding device 127 further includes an annular channel 134 around the perimeter of the short straight tubular distal section 131 and a longitudinal groove 135 which extends along the side of shaft 130 from annular channel 134 to the proximal end 72 of the shaft.

The balloon assembly comprises a hollow, expansible member 80 generally toroidal in shape having an inlet 80A, and means to expand the expansible member comprising an inflation device 107 in fluid communication with the inlet 80A of the expansible member 80 through an elongate tube 81. The inflation device 107 is the same as the inflation device described in the embodiment of the present invention shown in FIGS. 18–21 and is operable to introduce fluid into the expansible member to expand it radially outwardly relative to the shaft and further to permit deflation of the expansible member. Expansible member 80 is made of a resilient material and is capable of being slipped over blunt end 14 to be removably seated in annular channel 134. Thus, the balloon assembly can be removed or installed to allow the user to replace the assembly from the suture guiding device 128 after every suturing procedure. Tube 81 is attached to the inlet 80A of the expansible member 80 and is disposed in longitudinal groove 135 along its entire length. At the proximal end of tube 81, inflation device 107 is attached. The inflator 107A of the inflation device 107 supplies fluid 106 under pressure into tube 81 which guides fluid 106 into expansible member 80 and expands it. The release valve (not shown) of the inflation device allows the expansible member 80 to deflate when so desired the user. As shown in FIGS. 34–37, when expansible member 80 expands, its inner wall 114 presses against the suture guiding device and its outer wall 115 presses against the urethral internal wall 30. The pressure of the expansible member 80 against the total perimeter of the urethral internal wall 30 will also provide pressure to the dorsal vein complex 117 and the lateral vascular bundle 118. This pressure helps to stop hemorrhaging of a severed urethra and also the bleeding of the urethra stump 116 during a suturing procedure. As shown in FIG. 38, a secondary use of this internal pressure is to keep the suture guiding device from slipping through the urethral internal wall 30. As the surgeon pushes the suture guiding device, with the expansible member expanded, deeper into the urethral meatus, the suture guiding device will cause eversion of the urethral stump, carrying the urethra stump 116 away from the surrounding tissue 23. Exposing the urethral stump 116 will provide the surgeon a better view so that sutures can be placed in the most desired locations.

FIGS. 44 through FIG. 57 illustrate a suturing system for impeding the flow of blood around a suturing site. The suturing system 205 comprises a suturing instrument in the form of a hemorrhagic control implement 182 and a flexible suture guiding obturator 206. This suturing guiding system will allow the surgeon to better control hemorrhage during radical prostatectomy procedure.

Figure 53:
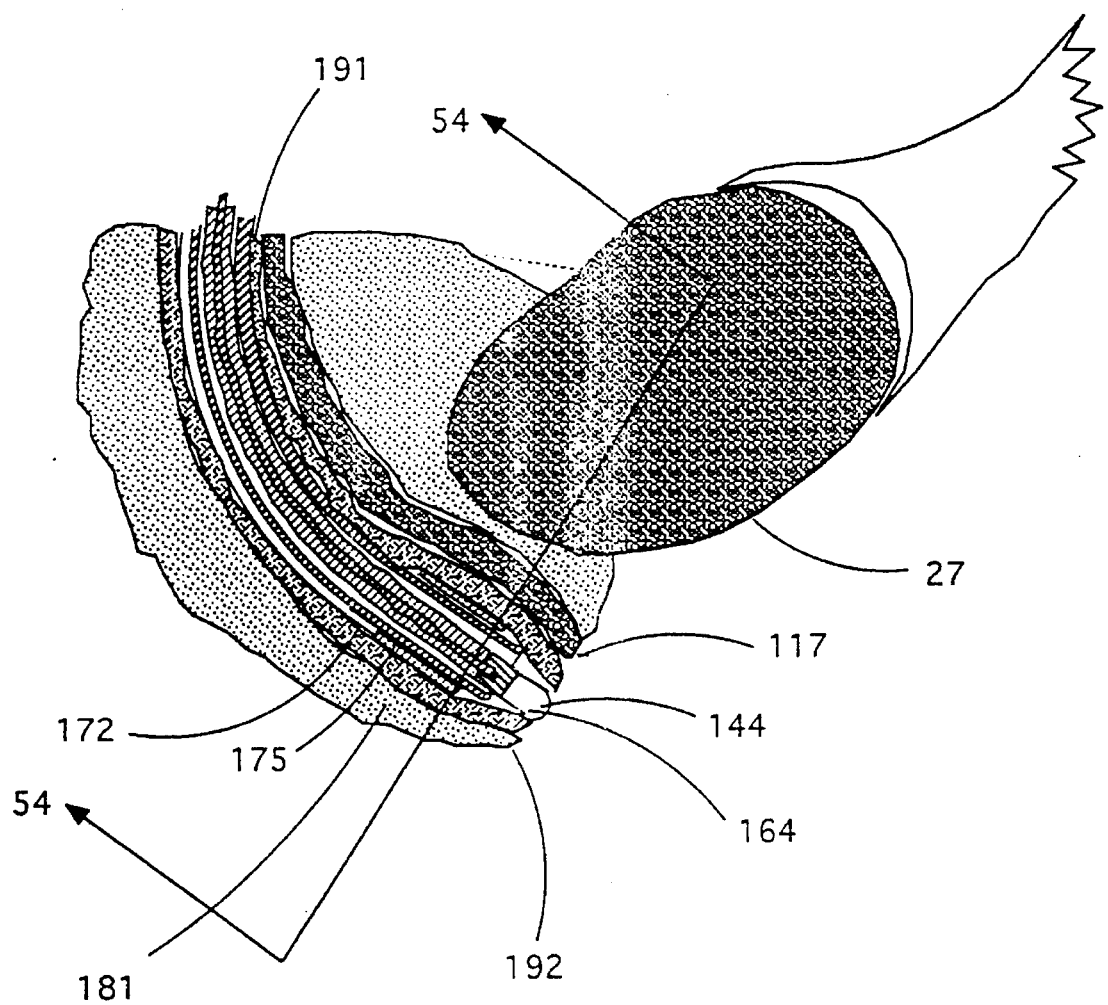
FIG. 53 is a partial cross section of the suturing instrument shown in FIG. 49 inside the urethra prior to inflation of its expansible member.
Figure 54:
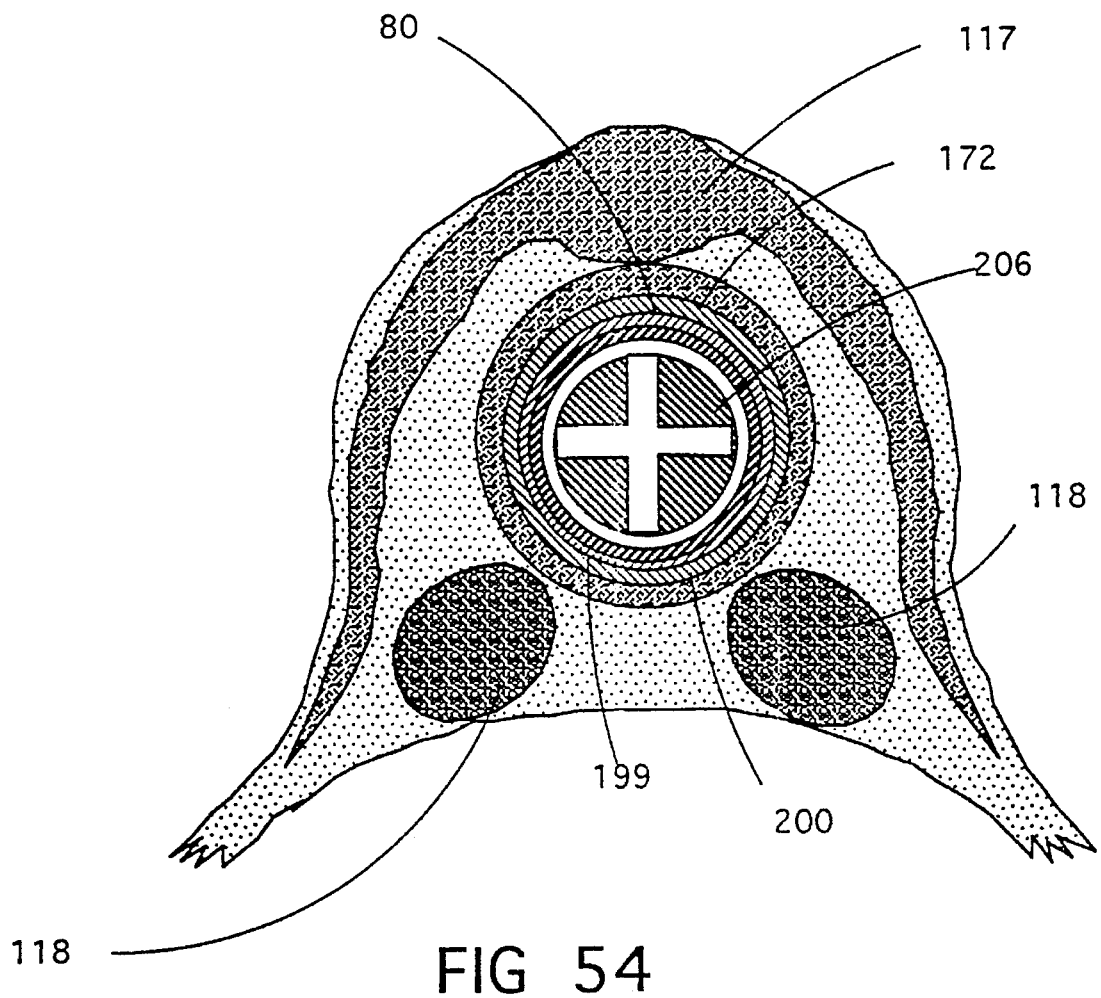
FIG. 54 is a sectional view taken along line 54—54 of FIG. 53.
Figure 55:
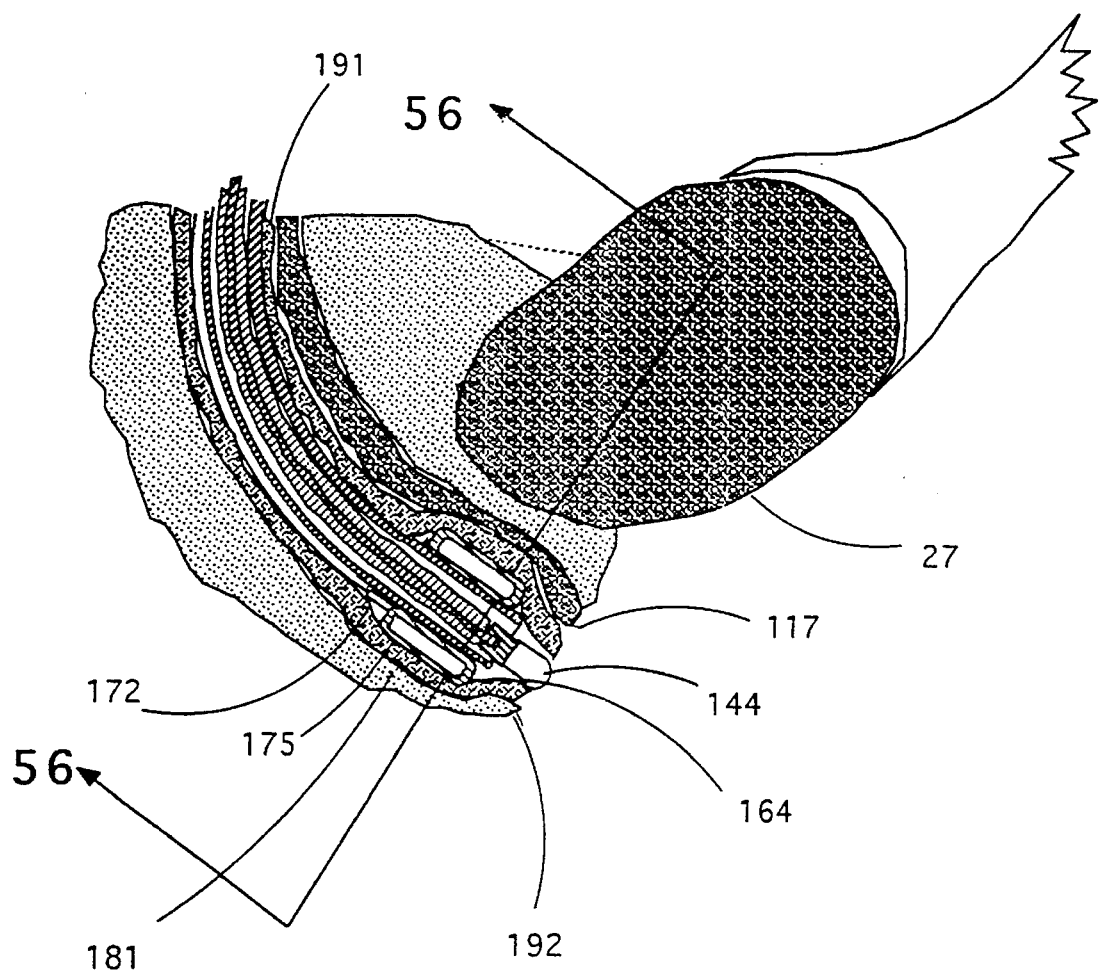
FIG. 55 is a partial cross section of the suturing instrument shown in FIG. 49 inside the urethra after inflation of the expansible member.
Figure 56:
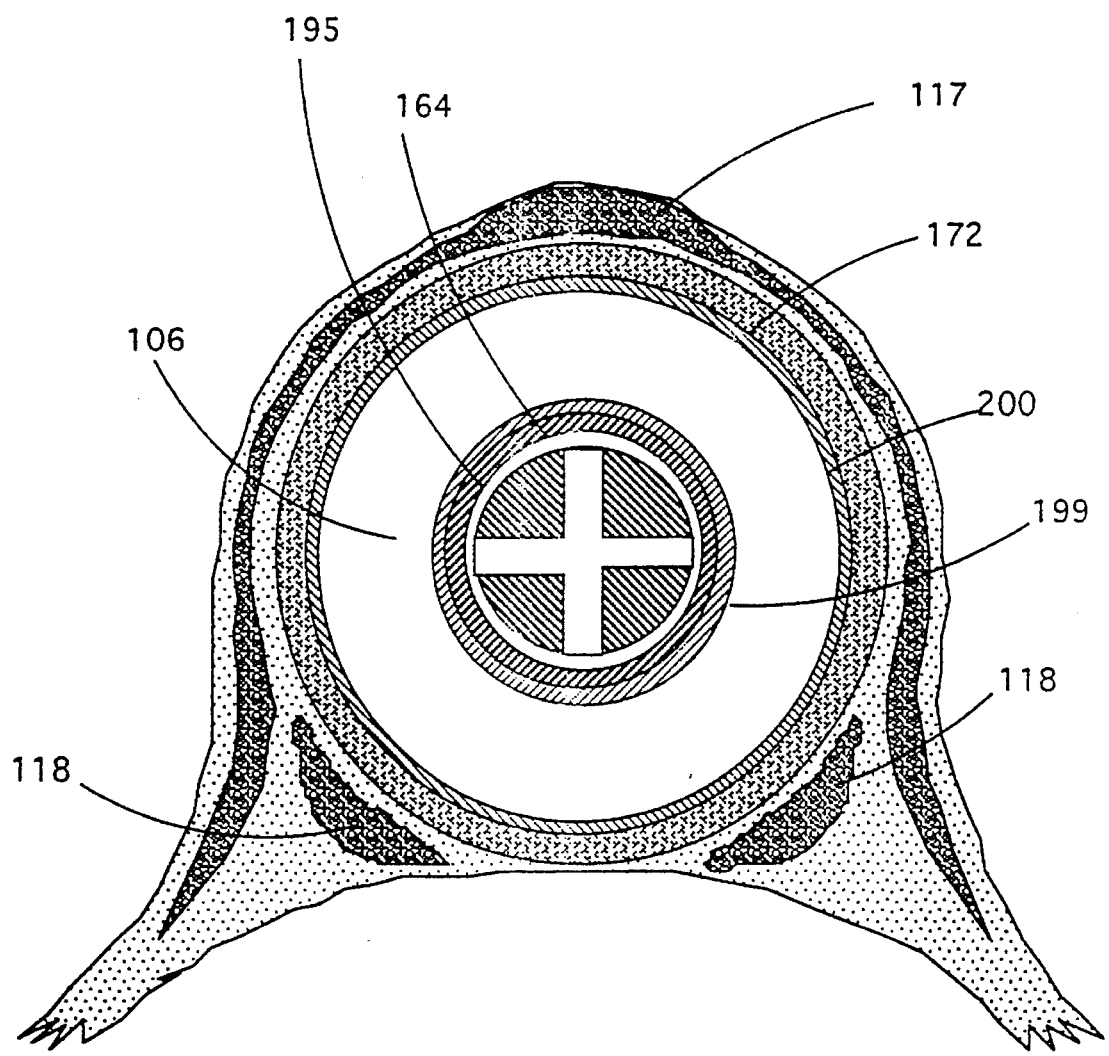
FIG. 56 is a sectional view taken along line 56—56 of FIG. 55.

FIGS. 44–47 show the hemorrhagic control implement 182 as comprising two components; an outer sheath 183 and the balloon assembly 184. The outer sheath 183 comprises a tubular, preferably bent shaft 185 having opposite ends which are distal 186 and proximal 187 relative to a person holding the device for use in a suturing procedure, the distal end 186 of the shaft being adapted to be inserted into a patient during the procedure. The tubular shaft 185 has a short, straight tubular distal section 188, followed by a curved tubular section 189, followed by a long, straight tubular section 190. An elongate passageway extends the full length of the shaft for receiving a standard Foley catheter or of a flexible suture guiding obturator 206 shown in FIG. 48. When the hemorrhagic control implement 182 is in use, the tubular shaft 185 must be capable of being manually grasped at the long, straight tubular section 190, and kept in control by the surgeon while inserted into the urethral meatus and guided all the way through the urethra 191 to eventually protrude out of the urethral stump 192, as shown in FIG. 53 and 55, in the same manner as a standard urethral sound is used. In addition, shaft 185 of the guiding sheath has an annular channel 193 around the perimeter of the short straight tubular distal section 188 and a longitudinal groove 194 which extends the length of tubular shaft 185 from channel 193 to the proximal end 187 of the shaft.

The balloon assembly 184 of the hemorrhagic control implement 182 is made up of an expansible annular member 195 of flexible, resilient material encircling the shaft adjacent its distal end 188, and expansion means comprising a tube 196 and an inflation device 197 for expanding the annular member radially outwardly relative to the shaft to impede the flow of blood around a suturing site. Expansible member 195 is capable of being slipped over the short straight tubular distal section 188 to be removably seated in groove 193. Thus, balloon assembly 184 can be removed to allow the user to replace the balloon assembly from the hemorrhagic control implement 182 after every suturing procedure. The tube 196 is attached to an inlet 195A of the expansible member 195 and is disposed in the groove 194 along its entire length. At the proximal end of tube 196, a standard inflation device 197 is attached. This inflation device 197 is the same as inflation device 107 described in the embodiment of the present invention shown in FIGS. 18–21. The inflator 197A of the inflation device 197 supplies fluid 198 under pressure into tube 196 which guides the fluid into expansible member 195 and expands the member. The release valve (not shown) allows the expansible member to deflate when so desired by the user. As shown in FIGS. 53–56, when the expansible member 195 expands, its inner wall 199 presses against the guiding device and its outer wall 200 presses against the urethral internal wall 172. The pressure of the expansible member 195 against the total perimeter of the urethral internal wall 172 will also provide pressure to the dorsal vein complex 117 and the lateral vascular bundle 118. This pressure helps to stop the flow of blood through the dorsal vein complex 117 and lateral vascular bundle 118, and allows the surgeon to cut and separate the urethra from the prostate gland during radical prostatectomy without tying individual suture on the dorsal vein complex 117 and the lateral vascular bundle 118.

Figure 48:
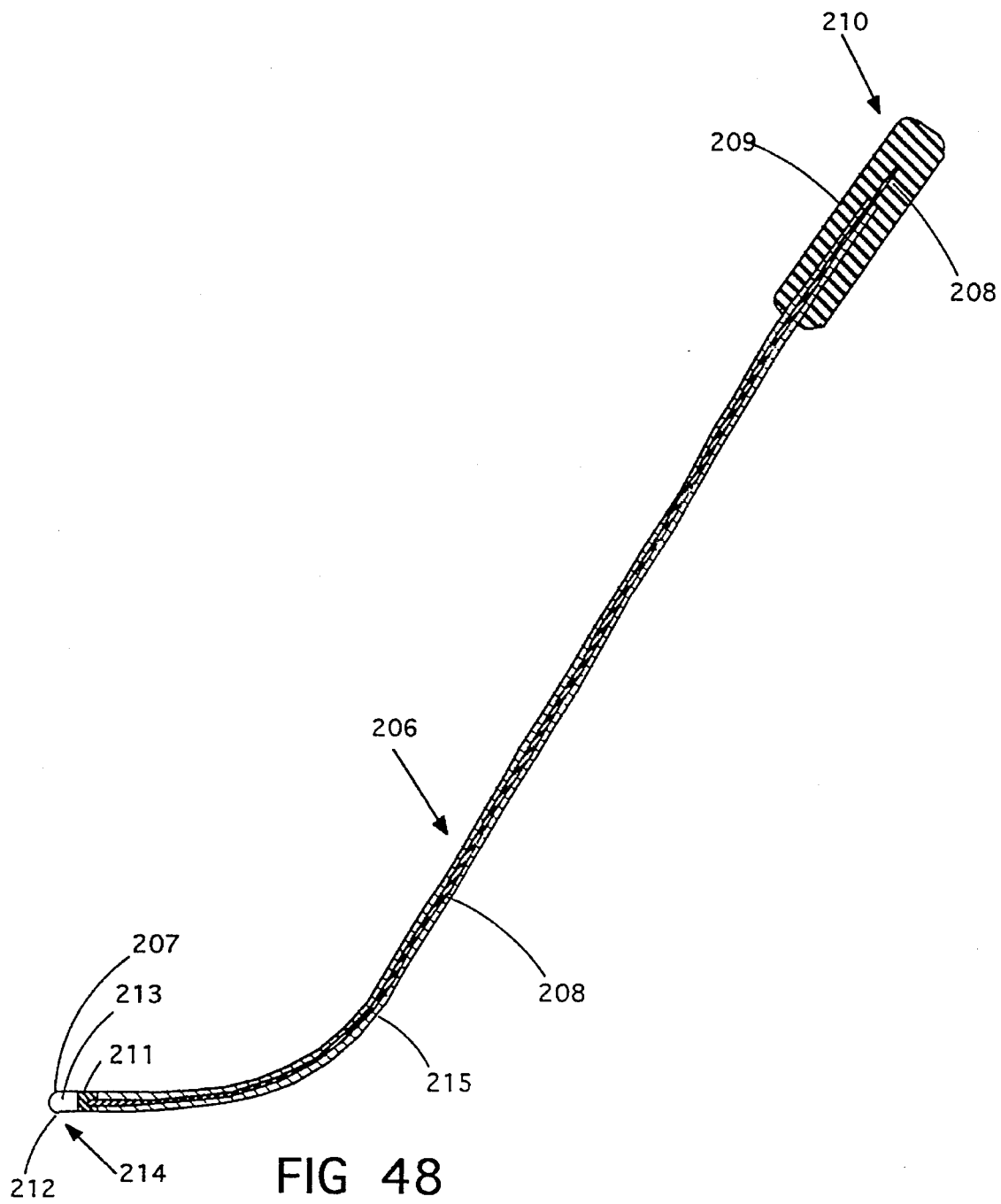
FIG. 48 is a vertical section of a flexible obturator that is used with the suturing instrument of the present invention shown in FIG. 44.

FIGS. 49–52 show the suture guiding system 205 with a flexible suture guiding obturator 206 extending through the passageway 201 of the hemorrhagic control implement 182. As shown in FIG. 48, the flexible suture guiding obturator 206 comprises an elongate flexible shaft 208 of circular cross section, a handle 209 mounted on the shaft of the obturator generally adjacent its proximal end 210, and a suture guide 212 mounted on the shaft of the obturator at its distal end 214 having a slit 213 lying in a plane extending endwise relative to short section 211 at the distal end 214 of the obturator. This slit 213 is generally channel-shaped and extends endwise proximally inwardly from the distal end 214 of the shaft 208 of the obturator and laterally across the suture guide from one side of the guide to an opposite side of the guide. The slit 213 has a guide surface configured for guiding a suture needle pulling a suture thread as it passes through the guide from one side of the guide to the opposite side of the guide. In this embodiment, the sutures can be placed around the urethral stump and thus the slit 213 has the same function and advantages as the slit of applicant's externally controlled, rotational suture guiding device disclosed in the above-referenced copending application by specifically allowing the curved needle 20 to enter the urethral internal wall 30 near perpendicularly (FIG. 38). This causes the needle 20 to head in an exit direction the moment it starts to penetrate the urethral internal wall 30. Obturator 206 is further covered with a flexible material 215 to make the cross-sectional diameter of the shaft 208 substantially the same as the diameter of short shaft section 211. This extra material prevents the flexible shaft from buckling when the flexible suture guiding obturator 206 is pushed inside the hemorrhagic control implement 182. The short shaft section 211 diameter must be as large as possible but small enough to slide inside the curved tubular section 189.

In operation, the hemorrhagic control implement 182 of the suturing system is advanced with a standard Foley catheter (not shown) in place to the urethro-prostatic junction. The position of the hemorrhagic control implement 182 can be confirmed by digital palpation through the rectum. A step off from the Foley catheter to the hemorrhagic control implement 182 would allow the surgeon to localize the distal end of the suturing instrument 182 and thus confirm the proper position of the instrument. The expansible member 195 of the hemorrhagic control implement is inflated with fluid 198 to expand and compress the membranous urethra and its surrounding tissue 181 including the dorsal vein complex 117 and the lateral vascular bundle 118. Once the hemorrhagic control implement 182 is in place, the Foley catheter can be advanced into the bladder and inflated to hold the catheter in place.

The retropubic prostatectomy is proceeded using the standard technique with following modification: the dorsal vein complex overlying the anterior surface of the prostate gland is ligated using one or two suture ligatures. This will control the back bleeding. The dorsal vein complex can then divide distal to the ligating suture. The dorsal vein complex anterior to the urethra should not bleed despite the division for it is controlled with the pressure provided by the expansible member 195. If the pressure provided by the expansible member alone does not result in satisfactory hemostasis the hemorrhagic control implement 182 can be lifted superiorly to compress the dorsal vein complex 117 against the under surface of the pubic symphysis and stop any bleeding. This portion of the dorsal vein complex can then be suture ligated in a bloodless field. Once the dorsal vein complex is divided, the prostate gland can be divided from the urethra at the urethral-prostatic junction. The prostatectomy can then be completed in the standard fashion.

Figure 57:
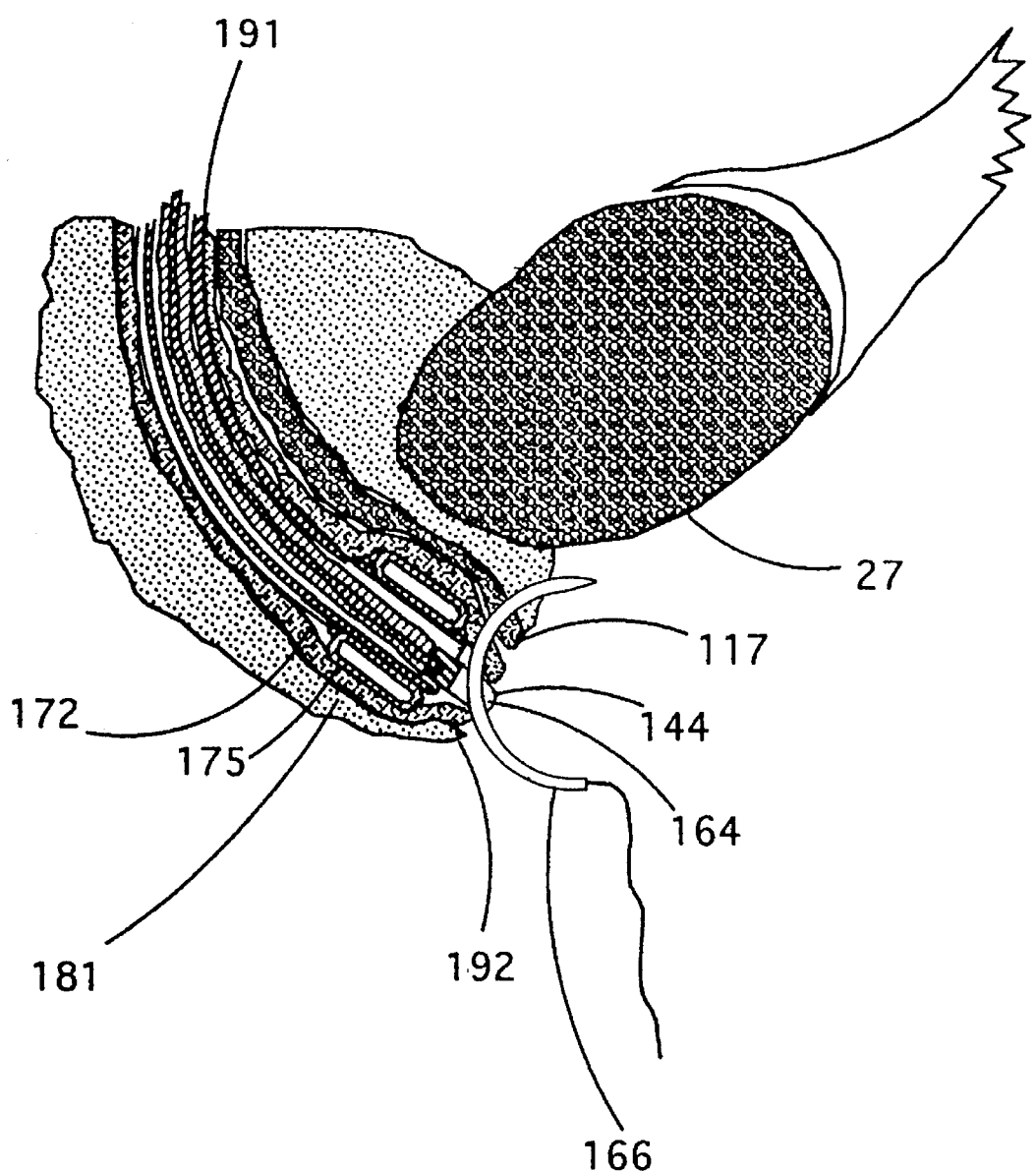
FIG. 57 is a partial cross section of the suturing instrument shown in FIG. 49 inside the urethra while the suture is being guided.

The Foley catheter is removed during radical prostatectomy. Following reconstruction of the bladder neck, the flexible suture guiding obturator 206 shown in FIG. 48, is passed through the passageway of the hemorrhagic control implement 182 as shown in FIGS. 49–52. The suture guide 207 of the obturator is allowed to protrude a few millimeters out of the urethral stump 192. The hemorrhagic control implement is then advanced toward the pelvis. Because of the interference fit of the expanded expansible member of the hemorrhagic control implement and the urethral lumen, advancing the hemorrhagic control implement causes the edge of the urethral stump to be advanced or everted into the pelvis, as shown in FIG. 57. The anastomosing suture can then be placed in desired location through the suture guiding grooves. The procedure is then completed in standard fashion.

This invention has been tested and found to be satisfactory for the accomplishment of the above objectives. While we have shown preferred embodiments thereof, we wish it to be specifically understood that our suturing instruments may take other forms without departing from the scope of our invention. For example, the control knob can be of different sizes and shapes, and it may have a narrow section spinning inside a tubular shaft with a large inside diameter at the control knob end.

It is also obvious that all sharp edges should be removed from the slit to protect the urethral internal wall.

It will also be understood that the configuration and number of slits in the suture guide of our instruments may vary. For example, more than one or two slits may be provided, and the slits may be arranged at any angle relative to one another. The cross sectional shapes of a slit may also vary from the shapes shown in the drawings.

Our suturing instruments can be made of many kinds of materials. Stainless steel is best for reusable suture guides but for disposable suture guides, plastic, aluminum or a combination of both will do the job.

What is claimed is:

1. A suturing instrument for impeding the flow of blood around a suturing site, the instrument comprising,
   a rigid bent shaft having opposite ends which are distal and proximal relative to a person holding the instrument, the distal end of the shaft being adapted to be inserted into a patient during said procedure,
   a suture guide at the distal end of the shaft,
   an expansible annular member of flexible, resilient material encircling the shaft adjacent its distal end, and
   expansion means for expanding said annular member radially outwardly relative to the shaft, said expansion means being adapted for expanding said annular member when the suturing instrument is positioned in the patient thereby to compress blood vessels adjacent said suturing instrument to occlude the flow of blood around a suturing site.

2. A suturing instrument as set forth in claim 1 wherein said annular member is a hollow member generally toroidal in shape having an inlet, and wherein said expansion means comprises an inflation device in fluid communication with said inlet of the annular member, said inflation device being operable to introduce fluid into the annular member to expand it radially outwardly relative to the shaft.

3. A suturing instrument as set forth in claim 2 wherein said shaft has an annular channel adjacent its distal end encircling the shaft, and wherein said annular member is seated in said channel.

4. A suturing instrument as set forth in claim 3 wherein said inflation device is mounted adjacent said proximal end of the shaft, and wherein said expansion means further includes a conduit for conveying fluid from the inflation device to the inlet of the annular member.

5. A suturing instrument as set forth in claim 4 wherein the shaft has a groove extending longitudinally along the shaft from said annular channel to said proximal end of the shaft, and wherein said conduit comprises an elongate tube disposed in the groove having a proximal end in fluid communication with the inflation device and a distal end in fluid communication with the inlet of said annular member.

6. A suturing instrument as set forth in claim 5 wherein said tube and said annular member are of one-piece construction.

7. A suturing instrument as set forth in claim 5 further comprising a longitudinal passageway extending through the shaft from its proximal end to its distal end for insertion of a medical implement therethrough for use in the suturing procedure.

8. A suturing instrument as set forth in claim 4 wherein said conduit comprises a longitudinal passageway extending through the shaft from its proximal end to its distal end, the longitudinal passageway having a proximal end in fluid communication with said inflation device and a distal end in fluid communication with said annular channel for conveying fluid from said inflation device to the inlet of said annular member.

9. A suturing instrument as set forth in claim 2 wherein the instrument further comprises at least one outwardly opening, generally channel-shaped end slit in the suture guide extending endwise proximally inwardly from the distal end of the shaft and laterally across the shaft from one side of the shaft to an opposite side of the shaft, said end slit having a guide surface configured for guiding a suture needle pulling a suture thread as it passes through said guide from one side of the guide to said opposite side of the guide.

10. A suturing instrument as set forth in claim 2 wherein the suture guide is mounted at the distal end of the shaft for rotation relative to the shaft about an axis extending endwise with respect to the shaft, said guide having a guide surface configured for guiding a curved suture needle in a desired direction as the needle is pushed along the surface, a hand-operable control device mounted on the shaft generally adjacent its proximal end, and means interconnecting said guide and said control device whereby hand-operation of said control device effects rotation of the guide to selectively adjust the suture-guiding position of said guide surface.

11. A suturing instrument as set forth in claim 1 wherein said shaft comprises an elongate body and a retractable head at the distal end of the body, the head having a distal end portion forming said suture guide and a proximal end portion, the proximal end portion of the head having a diameter smaller than that of the distal end portion of the head, said annular member encircling said proximal end portion of the head, and wherein said expansion means comprises means for retracting the head in a proximal direction relative to the body of the shaft to squeeze said annular member between said distal end portion of the head and said body of the shaft to cause the annular member to expand radially outwardly relative to the shaft.

12. A suturing instrument as set forth in claim 11 further comprising a tubular guide mounted at the distal end of the body, said proximal end portion of the retractable head having a sliding fit in the guide to permit retraction of the head relative to the body.

13. A suturing instrument as set forth in claim 11 wherein said retracting means comprises a control knob rotatable on the shaft and a cable extending inside the shaft connected at one end to the control knob and at its other end to the retractable head, the arrangement being such that rotation of said control knob causes said cable to be pulled toward said proximal end of the shaft and the retractable head to retract relative to the body of the shaft.

14. A suturing instrument as set forth in claim 11 wherein said suture guide has at least one outwardly opening, generally channel-shaped end slit extending endwise proximally inwardly from the distal end of the head and laterally across the head from one side of the head to an opposite side of the head, said end slit having a guide surface configured for guiding a suture needle pulling a suture thread as it passes through said guide from said one side of the head to said opposite side of the head.

15. A suturing instrument for impeding the flow of blood around a suturing site, the instrument comprising, a rigid bent shaft having opposite ends which are distal and proximal relative to a person holding the instrument, the distal end of the shaft being adapted to be inserted into a patient during a suturing procedure, a passageway in the shaft extending the full length of the shaft to permit insertion of a medical instrument comprising a suture guide through the passageway for use in said suturing procedure, an expansible annular member of flexible, resilient material encircling the shaft adjacent its distal end, and expansion means for expanding said annular member radially outwardly relative to the shaft, said expansion means being adapted for expanding said annular member when the suturing instrument is positioned in the patient thereby to compress blood vessels adjacent said suturing instrument to occlude the flow of blood around a suturing site.

16. A suturing instrument as set forth in claim 15 wherein said annular member is a hollow member generally toroidal in shape having an inlet, and wherein said expansion means comprises an inflation device in fluid communication with said inlet of the annular member, said inflation device being operable to introduce fluid into the annular member to expand it radially outwardly relative to the shaft.

17. A suturing instrument as set forth in claim 16 wherein said shaft has an annular channel adjacent its distal end encircling the shaft, and wherein said annular member is seated in said channel.

18. A suturing instrument as set forth in claim 17 wherein said inflation device is mounted adjacent said proximal end of the shaft, and wherein said expansion means further includes a conduit for conveying fluid from the inflation device to the inlet of the annular member.

19. A suturing instrument as set forth in claim 18 wherein the shaft has a groove extending longitudinally along the shaft from said annular channel to said proximal end of the shaft, and wherein said conduit comprises an elongate tube disposed in the groove having a proximal end in fluid communication with the inflation device and a distal end in fluid communication with the inlet of said annular member.

20. A suturing instrument as set forth in claim 19 wherein said tube and said annular member are of one-piece construction.

21. The combination of a suturing instrument for impeding the flow of blood around a suturing site and an obturator, the suturing instrument comprising a bent shaft having opposite ends which are distal and proximal relative to a person holding inserted into a patient during a suturing procedure, a passageway in the shaft extending to full length of the shaft to permit insertion of a medical instrument through the passageway for use in said suturing procedure, an expansible annular member of flexible, resilient material encircling the shaft adjacent its distal end, and expansion means for expanding the annular member radially outwardly relative to the shaft to impede the flow of blood around a suturing site, the obturator comprising an elongate, flexible shaft having opposite ends which are distal and proximal relative to a person holding the obturator, a handle mounted on the shaft of the obturator generally adjacent its proximal end, a suture guide mounted on the shaft of the obturator at its distal end having at least one outwardly opening, generally channel-shaped end slit extending endwise proximally inwardly from the distal end of the shaft and laterally across the guide from one side of the guide to an opposite side of the guide, said end slit having a guide surface configured for guiding a suture needle pulling a suture thread as it passes through said guide from one side of the guide to said opposite side of the guide, the shaft of the obturator being adapted for insertion, distal end first, through the passageway of the suturing instrument to a position in which said suture guide extends distally beyond the distal end of the shaft of the suturing instrument and said handle is in a position where it may be manipulated to effect rotation of the suture guide relative to the suturing instrument about an axis extending endwise with respect to the distal end of the suturing instrument to selectively adjust the suture-guiding position of said guide surface.

22. A suturing system for impeding the flow of blood around a suturing site, the system comprising a suturing instrument comprising a shaft having opposite ends which are distal and proximal relative to a person holding the instrument, the distal end of the shaft being adapted to be inserted into a patient during a suturing procedure, a passageway in the shaft extending the full length of the shaft, an expansible annular member of flexible, resilient material encircling the shaft adjacent its distal end, and expansion means for expanding the annular member radially outwardly relative to the shaft to impede the flow of blood around a suturing site, and an obturator comprising an elongate, flexible shaft having opposite ends which are distal and proximal relative to a person holding the obturator, a handle mounted on the shaft of the obturator generally adjacent its proximal end, and a suture guide mounted on the shaft of the obturator at its distal end having at least one outwardly opening, generally channel-shaped end slit extending endwise proximally inwardly from the distal end of the shaft and laterally across the guide from one side of the guide to an opposite side of the guide, said end slit having a guide surface configured for guiding a suture needle pulling a suture thread as it passes through said guide from one side of the guide to said opposite side of the guide, the shaft of the obturator being adapted for insertion, distal end first, through the passageway of the suturing instrument to a position in which said suture guide extends distally beyond the distal end of the shaft of the suturing instrument and said handle is in a position where it may be manipulated to effect rotation of the suture guide relative to the suturing instrument about an axis extending endwise with respect to the distal end of the suturing instrument to selectively adjust the suture-guiding position of said guide surface.

* * * * *